(12) United States Patent
Woodard et al.

(10) Patent No.: US 6,250,880 B1
(45) Date of Patent: *Jun. 26, 2001

(54) ROTARY PUMP WITH EXCLUSIVELY HYDRODYNAMICALLY SUSPENDED IMPELLER

(75) Inventors: John C. Woodard, Thornleigh; Peter A. Watterson, West Ryde; Geoffrey D. Tansley, Normanhurst, all of (AU)

(73) Assignee: Ventrassist Pty. Ltd, Labrador (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/299,038

(22) Filed: Apr. 23, 1999

Related U.S. Application Data

(63) Continuation-in-part of application No. 09/281,608, filed on Mar. 30, 1999, which is a continuation of application No. PCT/AU98/00725, filed on Sep. 18, 1998.

(30) Foreign Application Priority Data

Sep. 5, 1997 (AU) .................................................. P09027

(51) Int. Cl.⁷ ............................... F03B 13/00; B63H 1/26
(52) U.S. Cl. ................. 415/182.1; 415/900; 416/223 R; 416/3
(58) Field of Search ................. 415/900, 182.1, 415/203, 224; 416/3, 223 R, 234, 235; 417/420

(56) References Cited

U.S. PATENT DOCUMENTS

| | | |
|---|---|---|
| 4,382,199 | 5/1983 | Isaacson . |
| 4,688,998 | 8/1987 | Olsen et al. ........................ 417/356 |
| 4,944,748 | 7/1990 | Bramm et al. ................... 417/356 X |
| 5,055,005 * | 10/1991 | Kletschka ............................. 417/356 |
| 5,112,200 | 5/1992 | Isaacson et al. . |
| 5,145,333 * | 9/1992 | Smith ................................ 415/900 X |
| 5,147,187 * | 9/1992 | Ito et al. ....................... 416/223 R X |
| 5,195,877 * | 3/1993 | Kletschka ............................. 417/356 |
| 5,211,546 | 5/1993 | Isaacson et al. . |
| 5,326,344 * | 7/1994 | Bramm et al. ................... 417/356 X |
| 5,470,208 * | 11/1995 | Kletschka ............................. 417/356 |
| 5,685,700 * | 11/1997 | Izraelev ............................. 415/900 X |
| 5,725,357 * | 3/1998 | Nakazeki et al. ................ 415/900 X |
| 5,800,559 * | 9/1998 | Higham et al. ........................ 623/23 |
| 5,924,848 * | 7/1999 | Izraelev ............................. 415/900 X |
| 5,938,412 * | 8/1999 | Izraelev ............................. 415/900 X |

FOREIGN PATENT DOCUMENTS

| | | |
|---|---|---|
| PO 9027 | 9/1997 | (AU) . |
| PCT/AU 98/00725 | 9/1998 | (AU) . |
| 3343-186 | 11/1983 | (DE) . |
| WO 88/07842 | 10/1988 | (EP) . |
| WO 91/19103 | 12/1991 | (EP) . |
| WO 94/13955 | 6/1994 | (EP) . |
| WO 00/32256 | 11/1999 | (WO) . |

* cited by examiner

Primary Examiner—John E. Ryznic
(74) Attorney, Agent, or Firm—Knobbe, Martens, Olson & Bear LLP

(57) ABSTRACT

A pump assembly 1, 33, 200 adapted for continuous flow pumping of blood. In a particular form the pump 1, 200 is a centrifugal pump wherein the impeller 100, 204 is entirely sealed within the pump housing 2, 201 and is exclusively hydrodynamically suspended therein as the impeller rotates within the fluid 105 urged by electromagnetic means external to the pump cavity 106, 203.

Hydrodynamic suspension is assisted by the impeller 100, 204 having deformities therein such as blades 8 with surfaces tapered from the leading edges 102, 223 to the trailing edges 103, 224 of bottom and top edges 221, 222 thereof.

49 Claims, 27 Drawing Sheets

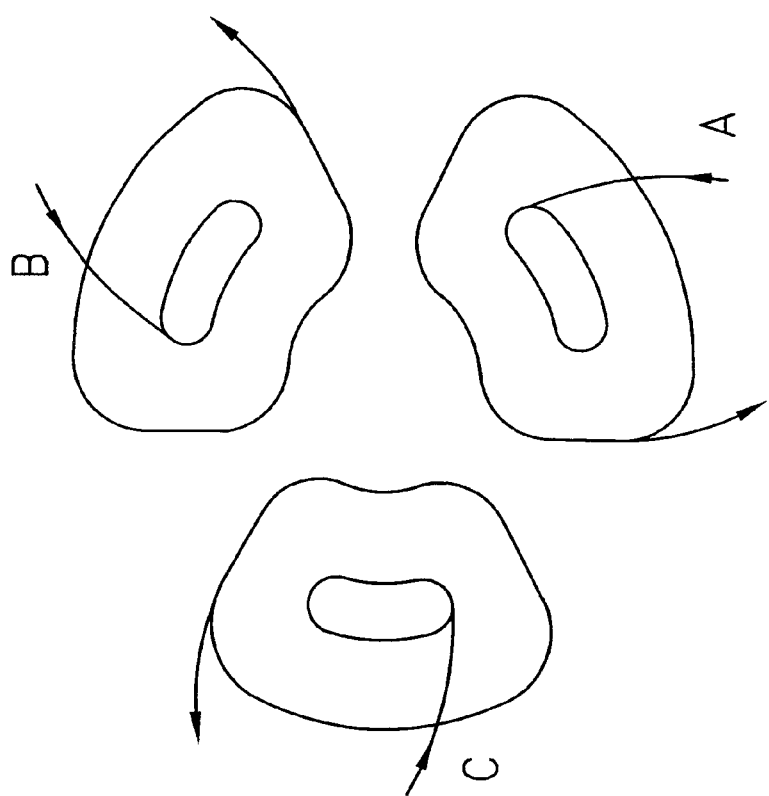

ROTARY PUMP WITH EXCLUSIVELY HYDRODYNAMICALLY SUSPENDED IMPELLER

This application is a continuation in part of application Ser. No. 09/281,608 filed Mar. 30, 1999 which is a continuation of PCT/AU98/00725 filed Sep. 18, 1998.

FIELD OF THE INVENTION

This invention relates to rotary pumps adapted, but not exclusively, for use as artificial hearts or ventricular assist devices and, in particular, discloses in preferred forms a seal-less shaft-less pump featuring open or closed (shrouded) impeller blades with at least parts of the impeller used as hydrodynamic thrust bearings and with electromagnetic torque provided by the interaction between magnets embedded in the blades or shroud and a rotating current pattern generated in coils fixed relative to the pump housing.

BACKGROUND ART

This invention relates to the art of continuous or pulsatile flow rotary pumps and, in particular, to electrically driven pumps suitable for use although not exclusively as an artificial heart or ventricular assist device. For permanent implantation in a human patient, such pumps should ideally have the following characteristics: no leakage of fluids into or from the bloodstream; parts exposed to minimal or no wear; minimum residence time of blood in pump to avoid thrombosis (clotting); minimum shear stress on blood to avoid blood cell damage such as haemolysis; maximum efficiency to maximise battery duration and minimise blood heating; and absolute reliability.

Several of these characteristics are very difficult to meet in a conventional pump configuration including a seal, i.e. with an impeller mounted on a shaft which penetrates a wall of the pumping cavity, as exemplified by the blood pumps referred to in U.S. Pat. No. 3,957,389 to Rafferty et al., U.S. Pat. No. 4,625,712 to Wampler, and U.S. Pat. No. 5,275,580 to Yamazaki. Two main disadvantages of such pumps are firstly that the seal needed on the shaft may leak, especially after wear, and secondly that the rotor of the motor providing the shaft torque remains to be supported, with mechanical bearings such as ball-bearings precluded due to wear. Some designs, such as U.S. Pat. No. 4,625,712 to Wampler and U.S. Pat. No. 4,908,012 to Moise et al., have overcome these problems simultaneously by combining the seal and the bearing into one hydrodynamic bearing, but in order to prevent long residence times they have had to introduce means to continuously supply a blood-compatible bearing purge fluid via a percutaneous tube.

In seal-less designs, blood is permitted to flow through the gap in the motor, which is usually of the brushless DC type, i.e. comprising a rotor including permanent magnets and a stator in which an electric current pattern is made to rotate synchronously with the rotor. Such designs can be classified according to the means by which the rotor is suspended: contact bearings, magnetic bearings or hydrodynamic bearings, though some designs use two of these means.

Contact or pivot bearings, as exemplified by U.S. Pat. No. 5,527,159 to Bozeman et al. and U.S. Pat. No. 5,399,074 to Nose et al., have potential problems due to wear, and cause very high localised heating and shearing of the blood, which can cause deposition and denaturation of plasma proteins, with the risk of embolisation and bearing seizure.

Magnetic bearings, as exemplified by U.S. Pat. No. 5,350,283 to Nakazeki et al., U.S. Pat. No. 5,326,344 to Bramm et al. and U.S. Pat. No. 4,779,614 to Moise et al., offer contactless suspension, but require rotor position measurement and active control of electric current for stabilisation of the position in at least one direction, according to Earnshaw's theorem. Position measurement and feedback control introduce significant complexity, increasing the failure risk. Power use by the control current implies reduced overall efficiency. Furthermore, size, mass, component count and cost are all increased.

U.S. Pat. No. 5,507,629 to Jarvik claims to have found a configuration circumventing Earnshaw's Theorem and thus requiring only passive magnetic bearings, but this is doubtful and contact axial bearings are included in any case. Similarly, passive radial magnetic bearings and a pivot point are employed in U.S. Pat. No. 5,443,503 to Yamane.

Prior to the present invention, pumps employing hydrodynamic suspension, such as U.S. Pat. No. 5,211,546 to Isaacson et al. and U.S Pat. No. 5,324,177 to Golding et al., have used journal bearings, in which radial suspension is provided by the fluid motion between two cylinders in relative rotation, an inner cylinder lying within and slightly off axis to a slightly larger diameter outer cylinder. Axial suspension is provided magnetically in U.S. Pat. No. 5,324,177 and by either a contact bearing or a hydrodynamic thrust bearing in U.S. Pat. No. 5,211,546.

A purging flow is needed through the journal bearing, a high shear region, in order to remove dissipated heat and to prevent long fluid residence time. It would be inefficient to pass all the fluid through the bearing gap, of small cross-sectional area, as this would demand an excessive pressure drop across the bearing. Instead a leakage path is generally provided from the high pressure pump outlet, through the bearings and back to the low pressure pump inlet, implying a small reduction in outflow and pumping efficiency. U.S. Pat. No. 5,324,177 provides a combination of additional means to increase the purge flow, namely helical grooves in one of the bearing surfaces, and a small additional set of impellers.

U.S. Pat. No. 5,211,546 provides 10 embodiments with various locations of cylindrical bearing surfaces. One of these embodiments, the third, features a single journal bearing and a contact axial bearing.

Embodiments of the present invention offer a relatively low cost and/or relatively low complexity means of suspending the rotor of a seal-less blood pump, thereby overcoming or ameliorating the problems of existing devices mentioned above.

SUMMARY OF THE INVENTION

According to one aspect of the present invention, there is disclosed a rotary blood pump for use in a heart assist device or like device, said pump having an impeller suspended in use within a pump housing exclusively by hydrodynamic thrust forces generated by relative movement of said impeller with respect to and within said pump housing.

Preferably at least one of said impeller or said housing includes at least one deformed surface which, in use, moves relative to a facing surface on the other of said impeller or said housing thereby to cause a restriction in the form of a reducing distance between the surfaces with respect to the relative line of movement of said deformed surface thereby to generate relative hydrodynamic thrust between said impeller and said housing which includes everywhere a localized thrust component substantially and everywhere normal to the plane of movement of said deformed surface with respect to said facing surface.

Preferably the combined effect of the localized normal forces generated on the surfaces of said impeller is to produce resistive forces against movement in three translational and two rotational degrees of freedom thus supporting the impeller for rotational movement within said housing exclusively by hydrodynamic forces.

Preferably said thrust forces are generated by blades of said impeller.

More preferably said thrust forces are generated by edges of said blades of said impeller.

Preferably said edges of said blades are tapered or nonplanar so that a thrust is created between the edges and the adjacent pump casing during relative movement therebetween.

Preferably said edges of said blades are shaped such that the gap at the leading edge of the blade is greater than at the trailing edge and thus the fluid which is drawn through the gap experiences a wedge shaped restriction which generates a thrust.

Preferably the pump is of centrifugal type or mixed flow type with impeller blades open on both front and back faces of the pump housing.

Preferably the front face of the housing is made conical, in order that the thrust perpendicular to the conical surface has a radial component, which provides a radial restoring force to a radial displacement of the impeller axis during use.

Preferably the driving torque of said impeller derives from the magnetic interaction between permanent magnets within the blades of the impeller and oscillating currents in windings encapsulated in the pump housing.

Preferably said blades include magnetic material therein, the magnetic material encapsulated within a biocompatible shell or coating.

Preferably said biocompatible shell or coating comprises a diamond coating or other coating which can be applied at low temperature.

Preferably internal walls of said pump which can come into contact with said blades during use are coated with a hard material such as titanium nitride or diamond coating.

Preferably said impeller comprises an upper conical shroud having said taper or other deformed surface therein and wherein blades of said impeller are supported below said shroud.

Preferably said impeller further includes a lower shroud mounted in opposed relationship to said upper conical shroud and whereas said blades are supported within said upper and said lower shroud.

Preferably said deformed surface is located on said impeller.

Preferably said deformed surface is located within said housing.

Preferably forces imposed on said impeller in use, other than hydrodynamic forces, are controlled by design so that, over a predetermined range of operating parameters, said hydrodynamic thrust forces provide sufficient thrust to maintain said impeller suspended in use within said pump housing.

Preferably at least one face of the housing is made conical, in order that the thrust perpendicular to it has a radial component, which provides a radial restoring force to a radial displacement of the impeller axis. Similarly, an axial displacement toward either the front or the back face increases the thrust from that face and reduces the thrust from the other face. Thus the sum of the forces on the impeller due to inertia (within limits), gravity and any bulk radial or axial hydrodynamic force on the impeller can be countered by a restoring force from the thrust bearings after a small displacement of the impeller within the housing relative to the housing in either a radial or axial direction.

In a preferred embodiment, the impeller driving torque derives from the magnetic interaction between permanent magnets within the blades of the impeller and oscillating currents in windings encapsulated in the pump housing.

In a further broad form of the invention there is provided a rotary blood pump having an impeller suspended exclusively hydrodynamically by thrust forces generated by the impeller during movement in use of the impeller.

Preferably said thrust forces are generated by blades of said impeller or by deformities therein.

More preferably said thrust forces are generated by edges of said blades of said impeller.

Preferably said edges of said blades are tapered.

In an alternative preferred form said pump is of axial type.

Preferably within a uniform cylindrical section of the pump housing, tapered blade edges form a radial hydrodynamic bearing.

In a further broad form of the invention there is provided a rotary blood pump having a housing within which an impeller acts by rotation about an axis to cause a pressure differential between an inlet side of a housing of said pump and an outlet side of the housing of said pump; said impeller suspended exclusively hydrodynamically by thrust forces generated by the impeller during movement in use of the impeller.

BRIEF DESCRIPTION OF THE DRAWINGS

Embodiments of the present invention will now be described, with reference to the accompanying drawings, wherein:

FIG. 3A is a cross-sectional view of an impeller blade taken generally along the line A—A of FIG. 2;

FIG. 3B is an enlargement of the blade-pump housing interface portion of FIG. 3A;

DETAILED DESCRIPTION OF PREFERRED EMBODIMENTS

The pump assemblies according to various preferred embodiments to be described below all have particular, although not exclusive, application for implantation in a mammalian body so as to at least assist, if not take over, the function of the mammalian heart. In practice this is performed by placing the pump assembly entirely within the body of the mammal and connecting the pump between the left ventricle and the aorta so as to assist left side heart function. It may also be connected to the right ventricle and pulmonary artery to assist the right side of the heart.

In this instance the pump assembly includes an impeller which is fully sealed within the pump body and so does not require a shaft extending through the pump body to support it. The impeller is suspended, in use, within the pump body by the operation of hydrodynamic forces imparted as a result of the interaction between the rotating impeller, the internal pump walls and the fluid which the impeller causes to be urged from an inlet of the pump assembly to an outlet thereof.

Figure 1:
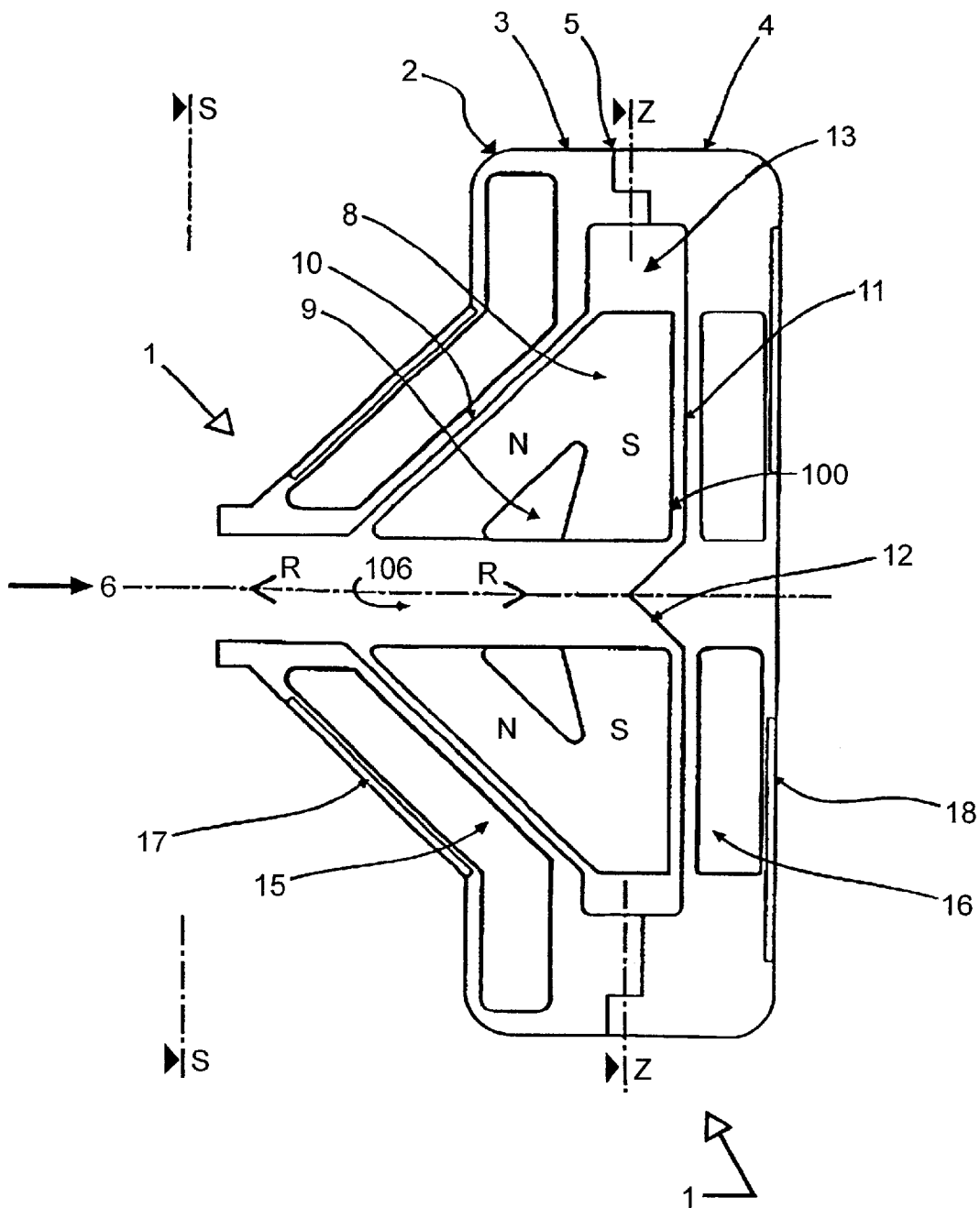
FIG. 1 is a longitudinal cross-sectional view of a preferred embodiment of the invention.
Figure 2:
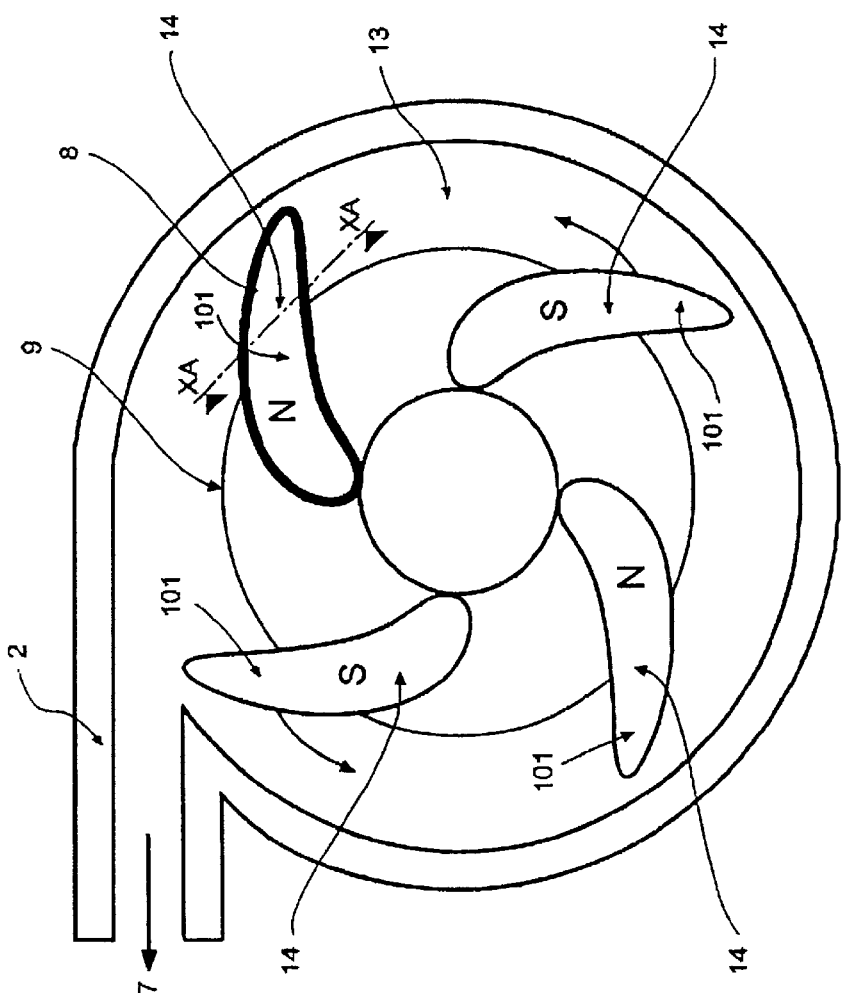
FIG. 2 is a cross-sectional view taken generally along the line Z—Z of FIG. 1.

A preferred embodiment of the invention is the centrifugal pump 1, as depicted in FIGS. 1 and 2, intended for implantation into a human, in which case the fluid referred to below is blood. The pump housing 2, can be fabricated in two parts, a front part 3 in the form of a housing body and a back part 4 in the form of a housing cover, with a smooth join therebetween, for example at 5 in FIG. 1. The pump 1 has an axial inlet 6 and a tangential outlet 7. The rotating part 100 is of very simple form, comprising only blades 8 and a blade support 9 to hold those blades fixed relative to each other. The blades may be curved as depicted in FIG. 2, or straight, in which case they can be either radial or backswept, i.e. at an angle to the radius. This rotating part 100 will hereafter be called the impeller 100, but it also serves as a bearing component and as the rotor of a motor configuration as to be further described below whereby a torque is applied by electromagnetic means to the impeller 100. Note that the impeller has no shaft and that the fluid enters the impeller from the region of its axis RR. Some of the fluid passes in front of the support cone 9 and some behind it, so that the pump 1 can be considered of two-sided open type, as compared to conventional open centrifugal pumps, which are only open on the front side. Approximate dimensions found adequate for the pump 1 to perform as a ventricular assist device, when operating at speeds in the range 1,500 rpm to 4,000 rpm, are outer blade diameter 40 mm, outer housing average diameter 60 mm, and housing axial length 40 mm.

Figure 3C:
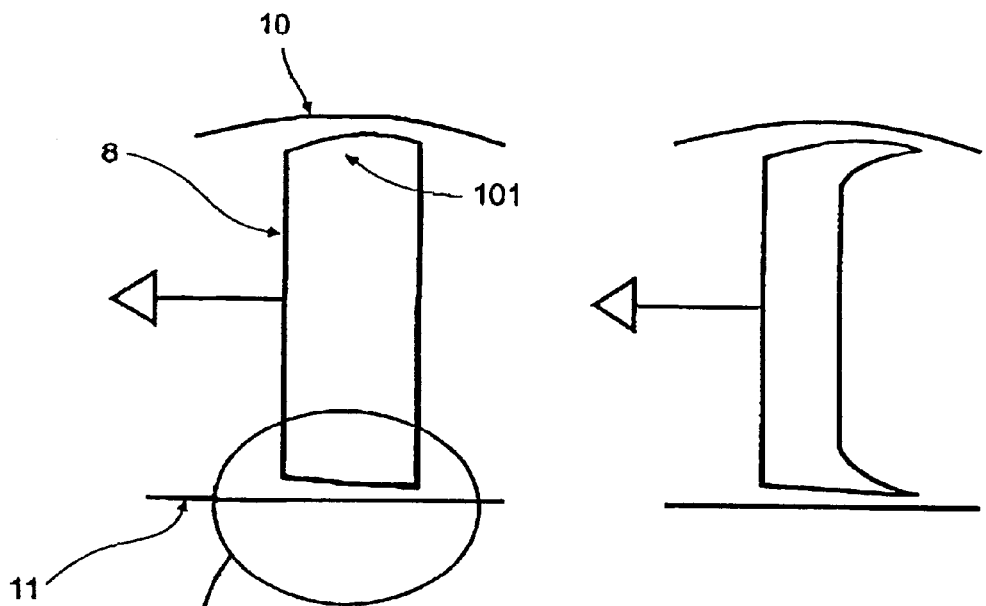
FIG. 3C is an alternative impeller blade shape.
Figure 3C:
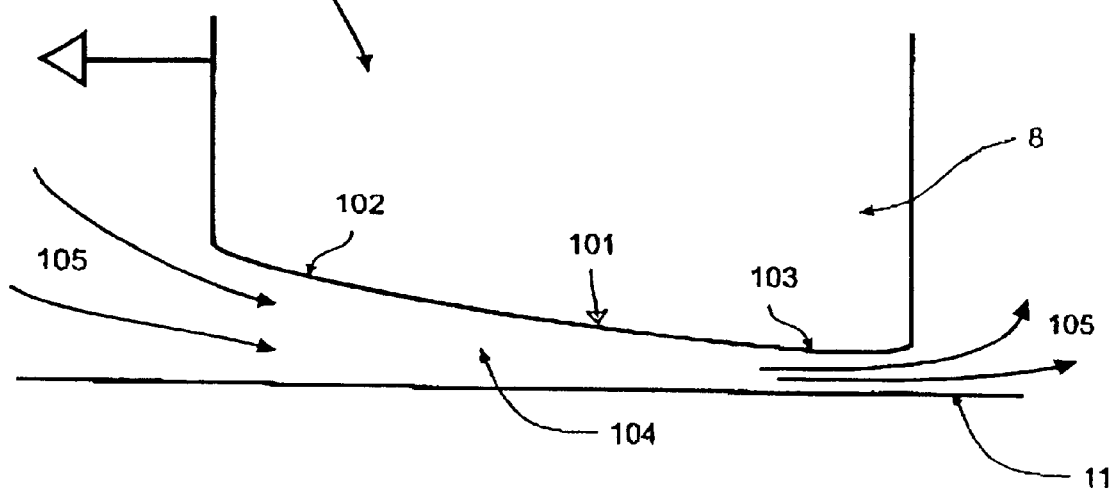

As the blades 8 move within the housing, some of the fluid passes through the gaps, much exaggerated in FIGS. 1 and 3, between the blade edges 101 and the housing front face 10 and housing back face 11. In all open centrifugal pumps, the gaps are made small because this leakage flow lowers the pump hydrodynamic efficiency. In the pump disclosed in this embodiment, the gaps are made slightly smaller than is conventional in order that the leakage flow can be utilised to create a hydrodynamic bearing. For the hydrodynamic forces to be sufficient, the blades may also be tapered as depicted in FIGS. 3A and 3B, so that the gap 104 is larger at the leading edge 102 of the blade 8 than at the trailing edge 103 thereby providing one example of a "deformed surface" as described elsewhere in this specification. The fluid 105 which passes through the gap thus experiences a wedge shaped restriction which generates a thrust, as described in Reynolds' theory of lubrication (see, for example, "Modern Fluid Dynamics, Vol. 1 Incompressible Flow", by N. Curle and H. J. Davies, Van Nostrand, 1968). For blades considerably thinner than their axial length, the thrust is proportional to the square of the blade thickness at the edge, and thus in this embodiment thick blades are favoured, since if the proportion of the pump cavity filled by blades is constant, then the net thrust force will be inversely proportional to the number of blades. However, the blade edges can be made to extend as tails from thin blades as depicted in FIG. 3C in order to increase the blade area adjacent the walls.

In one particular form, the tails join adjacent blades so as to form a complete shroud with wedges or tapers incorporated therein. An example of a shroud design as well as other variations on the blade structure will be described later in this specification.

For manufacturing simplicity, the housing front face 10 can be made conical, with an angle of around 45° so that it provides both axial and radial hydrodynamic forces. Other angles are suitable that achieve the functional requirements of this pump including the requirements for both axial and radial hydrodynamic forces.

Other curved surfaces are possible provided both axial and radial hydrodynamic forces can be produced as a result of rotation of the blades relative to the housing surfaces.

The housing back face 11 can include a roughly conical extension 12 pointing into the pump cavity 106, to eliminate or minimise the effect of the flow stagnation point on the axis of the back housing.

Alternatively extension 12 can resemble an impeller eye to make the flow mixed.

In this preferred embodiment, for manufacturing simplicity and for uniformity in the flow axial direction RR, the housing back face 11 is made flat over the bearing surfaces, i.e. under the blade edges. With this the case, a slacker tolerance on the alignment between the axes of the front part 3 and back part 4 of the housing 2 is permissible. An alternative is to make the back face 11 conical at the bearing surfaces, with taper in the opposite direction to the front face 10, so that the hydrodynamic forces from the back face will also have radial components. Tighter tolerance on the axes alignment would then be required, and some of the flow would have to undergo a reversal in its axial direction. Again a roughly conical extension (like 12) will be needed. There may be some advantage in making the housing surfaces and blade edges non-straight, with varying tangent angle, although this will impose greater manufacturing complexity.

There are several options for the shape of the taper, but in the preferred embodiment the amount of material removed simply varies linearly or approximately linearly across the blade. For the back face, the resulting blade edges are then planes at a slight inclination to the back face. For the front face, the initial blade edges are curved and the taper only removes a relatively small amount of material so they still appear curved. Alternative taper shapes can include a step in the blade edge, though the corner in that step would represent a stagnation line posing a thrombosis risk.

For a given minimum gap, at the trailing blade edge, the hydrodynamic force is maximal if the gap at the leading edge is approximately double that at the trailing edge. Thus the taper, which equals the leading edge gap minus the trailing edge gap, should be chosen to match a nominal minimum gap, once the impeller has shifted towards that edge. Dimensions which have been found to give adequate thrust forces are a taper of around 0.05 mm for a nominal minimum gap of around 0.05 mm, and an average circumferential blade edge thickness of around 6 mm for 4 blades. For the front face, the taper is measured within the plane perpendicular to the axis. The axial length of the housing between the front and back faces at any position should then be made about 0.2 mm greater than the axial length of the blade, when it is coaxial with the housing, so that the minimum gaps are both about 0.1 mm axially when the impeller 100 is centrally positioned within the housing 2. Then, for example, if the impeller shifts axially by 0.05 mm, the minimum gaps will be 0.05 mm at one face and 0.15 mm at the other face. The thrust increases with decreasing gap and would be much larger from the 0.05 mm gap than from the 0.15 mm gap, about 14 times larger for the above dimensions. Thus there is a net restoring force away from the smaller gap.

Similarly, for radial shifts of the impeller the radial component of the thrust from the smaller gap on the conical housing front face would offer the required restoring radial force. The axial component of that force and its torque on the impeller would have to be balanced by an axial force and torque from the housing back face, and so the impeller will also have to shift axially and tilt its axis to be no longer parallel with the housing axis. Thus as the person moves and the pump is accelerated by external forces, the impeller will continually shift its position and alignment, varying the gaps in such a way that the total force and torque on the impeller 100 match that demanded by inertia. The gaps are so small, however, that the variation in hydrodynamic efficiency will be small, and the pumping action of the blades will be approximately the same as when the impeller is centrally located.

While smaller gaps imply greater hydrodynamic efficiency and greater bearing thrust forces, smaller gaps also demand tighter manufacturing tolerances, increase frictional drag on the impeller, and impose greater shear stress an the fluid. Taking these points in turn, for the above 0.05 mm tapers and gaps, tolerances of around 0.005 mm are needed, which imposes some cost penalty but is achievable. A tighter tolerance is difficult, especially if the housing is made of a plastic, given the changes in dimension caused by temperature and possible absorption of fluid by plastic materials which may be in contact with the blood such as Acrylic of polyurethane. The frictional drag for the above gaps produces much smaller torque than the typical motor torque. Finally, to estimate the shear stress, consider a rotation speed of 3,000 rpm and a typical radius of 15 mm, at which the blade speed is 4.7 ms$^{-1}$ and the average velocity shear for an average gap of 0.075 mm is $6.2 \times 10^4$ s$^{-1}$. For blood of dynamic viscosity $3.5 \times 10^{-3}$ kgm$^{-1}$s$^{-1}$, the average shear stress would be 220 Nm$^{-2}$. Other prototype centrifugal blood pumps with closed blades have found that slightly larger gaps, e.g. 0.15 mm, are acceptable for haemolysis. A major advantage of the open blades of the present invention is that a fluid element that does pass through a blade edge gap will have very short residence time in that gap, around $2 \times 10^{-3}$ S, and the fluid element will most likely be swept though the pump without passing another blade edge.

With particular reference to FIGS. 3A and 3B typical working clearances and working movement for the impeller 8 with respect to the upper and lower housing surfaces 10, 11 is of the order of 100 microns clearance at the top and at the bottom. In use gravitational and other forces will bias the impeller 8 closer to one or other of the housing walls resulting, typically in a clearance at one interface of the order of 50 microns and a corresponding larger clearance at the other interface of the order of 150 microns. In use, likely maximum practical clearances will range from 300 microns down to 1 micron.

Typical restoring forces for a 25 gram rotor mass spinning at 2200 rpm are 1.96 Newtons at a 20 micron clearance extending to 0.1 Newtons at an 80 micron clearance.

To minimise the net force required of the hydrodynamic bearings, the net axial and radial hydrodynamic forces on the impeller from the bulk fluid flow should be minimised, where "bulk" here means other than from the bearing thrust surfaces.

The radial force on the impeller depends critically on the shape of the output flow collector or volute 13. The shape should be designed to minimise the radial impeller force over the desired range of pump speeds, without excessively lowering the pump efficiency. The optimal shape will have a roughly helical perimeter between the "cutwater" and outlet. The radial force can also be reduced by the introduction of an internal division in the volute 13 to create a second output flow collector passage, with tongue approximately diametrically opposite to the tongue of the first passage.

An indicative plan view of impeller 100 relative to housing 2 is shown in FIG. 2 having a concentric volute 13.

Figure 17:
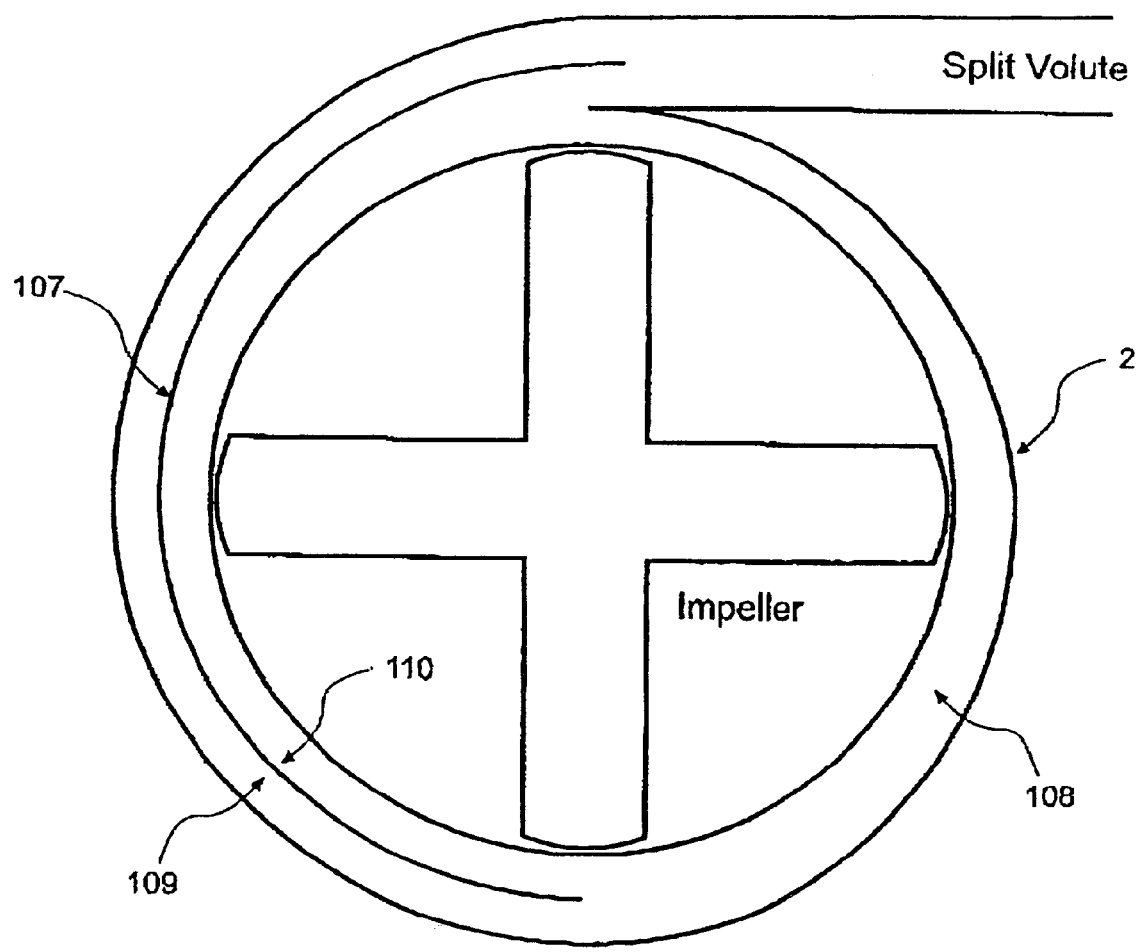
FIG. 17 is a plan, section view of a pump assembly showing an alternative volute arrangement.

FIG. 17 illustrates the alternative volute arrangement comprising a split volute created by volute barrier 107 which causes volute 108 in a first hemisphere of the housing 2 to split into first half volute 109 and second half volute 110 over the second hemisphere. The hemispheres are defined respectively on each side of a diameter of the housing 2 which passes through or near exit point 111 of outlet 7.

In alternative forms concentric volutes can be utilised, particularly where specific speed is relatively low.

In a further particular form a vaneless diffuser may also reduce the radial force.

In regard to the bulk hydrodynamic axial force, if the blade cross-section is made uniform in the axial direction along the rotational axis, apart from the conical front edge, then the pressure acting on the blade surface (excluding the bearing edges) will have no axial component. This also simplifies the blade manufacture. The blade support cone 9 must then be shaped to minimise axial thrust on the impeller and minimise disturbance to the flow over the range of speeds, while maintaining sufficient strength to prevent relative blade movement. The key design parameter affecting the axial force is the angle of the cone. The cone is drawn in FIG. 1 as having the same internal diameter as the blades, which may aid manufacture. However, the cone could be made with larger or smaller internal diameter to the blades. There may be advantage in using a non-axisymmetric support "cone", e.g. with larger radius on the trailing surface of a blade than the radius at the leading surface of the next blade. If the blades are made with non-uniform cross-section to increase hydrodynamic efficiency, then any bulk hydrodynamic axial force on them can be balanced by shaping the support cone to produce an opposite bulk hydrodynamic axial force on it.

Careful design of the entire pump, employing computational fluid dynamics, is necessary to determine the optimal shapes of the blades 8, the volute 13, the support cone 9 and the housing 2, in order to maximise hydrodynamic efficiency while keeping the bulk fluid hydrodynamic forces, shear and residence times low. All edges and the joins between the blades and the support cone should be smoothed.

The means of providing the driving torque on the impeller 100 of the preferred embodiment of the invention is to encapsulate permanent magnets 14 in the blades 8 of the impeller 100 and to drive them with a rotating magnetic field pattern from oscillating currents in windings 15 and 16, fixed relative to the housing 2. Magnets of high remanence such as sintered rare-earth magnets should be used to maximise motor efficiency. The magnets can be aligned axially but greater motor efficiency is achieved by tilting the magnetisation direction to an angle of around 15° to 30° outwards from the inlet axis, with 22.5° tilt suitable for a body of conical angle 45°. The magnetisation direction must alternate in polarity for adjacent blades. Thus there must be an even number of blades. Since low blade number is preferred for the bearing force, and since two blades would not have sufficient bearing stiffness to rotation about an axis through the blades and perpendicular to the pump housing (unless the blades are very curved), four blades are recommended. A higher number of blades, for example 6 or 8 will also work.

Figures 4A, 4B, 4C:
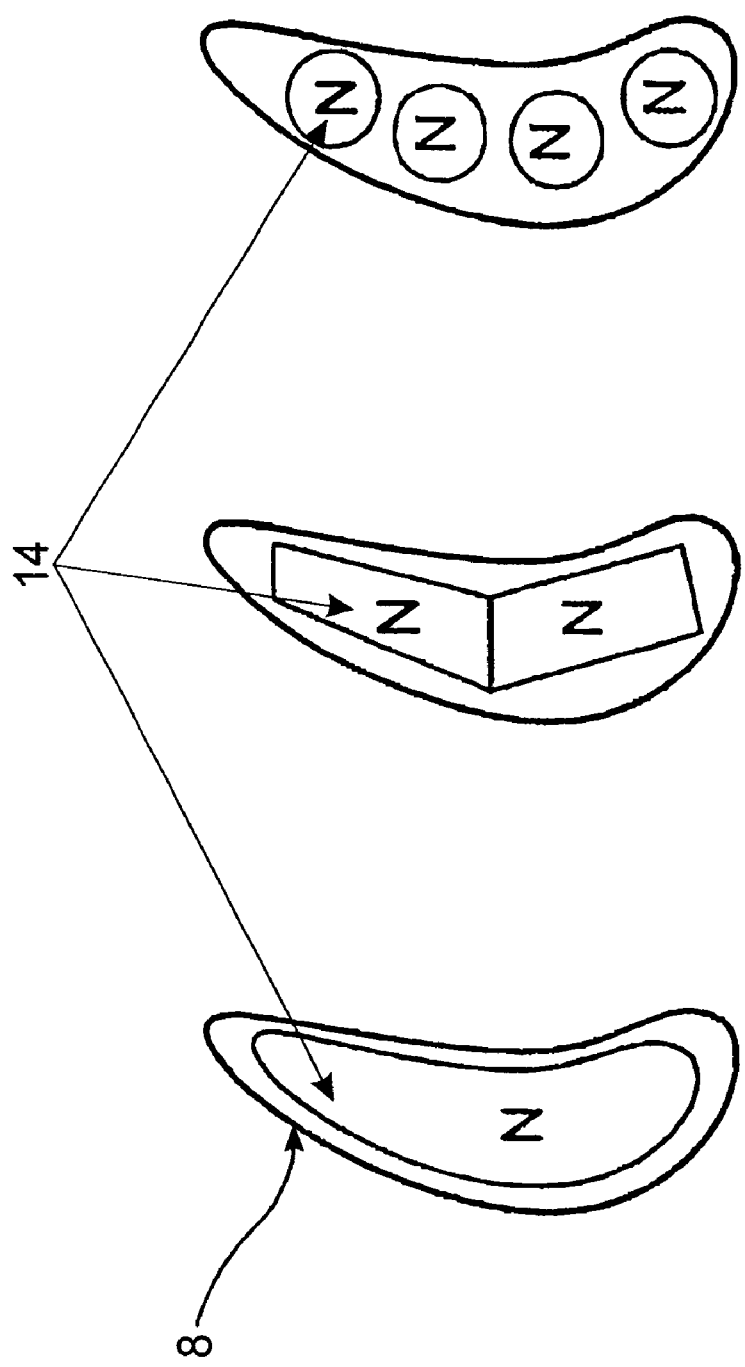
FIGS. 4A, B, C illustrate various possible locations of magnet material within a blade.

Some possible options for locating the magnets 14 within the blades 8 are shown in FIG. 4. The most preferred which is depicted in FIG. 4A, is for the blade to be made of magnet material apart from a biocompatible shell or coating to prevent fluid corroding the magnets and to prevent magnet material (which may be toxic) entering the blood stream. The coating should also be sufficiently durable especially at blade corners to withstand rubbing during start-up or during inadvertent bearing touch down.

In one particular form the inside walls of the pump housing 2 are also coated with a biologically compatible and wear resistant material such as diamond coating or titanium nitride so that wear on both of the touching surfaces is minimised.

An acceptable coating thickness is approximately 1 micron.

A suitable impeller manufacturing method is to die-press the entire impeller, blades and support cone, as a single axially aligned magnet. The die-pressing is much simplified if near axially uniform blades are used (blades with an overhang such as in FIG. 3C are precluded). During pressing, the crushed rare-earth particles must be aligned in an axial magnetic field. This method of die-pressing with parallel alignment direction is cheaper for rare-earth magnets, although it produces slightly lower remanence magnets. The tolerance in die-pressing is poor, and grinding of the tapered blade edges is required. Then the magnet impeller can be coated, for example by physical vapour deposition, of titanium nitride for example, or by chemical vapour deposition, of a thin diamond coating or a teflon coating.

In an alternative form the magnet material can be potted in titanium or a polymeric housing which is then, in turn, coated with a biologically compatible and tough material such as diamond coating or titanium nitride.

Finally, to create the alternating blade polarity the impeller must be placed in a special pulse magnetisation fixture, with an individual coil surrounding each blade. The support cone of a die-pressed magnet impeller acquires some magnetisation near the blades, with negligible influence.

Alternative magnet locations are sketched in FIG. 4B and FIG. 4C in which quadrilateral or circular cross-section magnets 14 are inserted into the blades. Sealing and smoothing of the blade edges over the insertion holes is then required to reinstate the taper.

All edges in the pump should be radiused and surfaces smoothed to avoid possible damage to formed elements of the blood.

The windings 15 and 16 of the preferred embodiment are slotless or air-gap windings with the same pole number as the impeller, namely four poles in the preferred embodiment. A ferromagnetic iron yoke 17 of conical form for the front winding and an iron ferromagnetic yoke 18 of annular form for the back winding may be placed on the outside of the windings to increase the magnetic flux densities and hence increase motor efficiency. The winding thicknesses should be designed for maximum motor efficiency, with the sum of their axial thicknesses somewhat less than but comparable to the magnet axial length. The yokes can be made of solid ferromagnetic material such as iron. To reduce "iron" losses, the yokes 17 can be laminated, for example in layers or by helically winding thin strip, or can be made of iron/powder epoxy composite. The yokes should be positioned such that there is zero net axial magnetic force on the impeller when it is positioned centrally in the housing. The magnetic force is unstable and increases linearly with axial displacement of the impeller away from the central position, with the gradient being called the negative stiffness of the magnetic force. This unstable magnetic force must be countered by the hydrodynamic bearings, and so the stiffness should be made as small as possible. Choosing the yoke thickness such that the flux density is at the saturation level reduces the stiffness and gives minimum mass. An alternative can be to have no iron yokes, completely eliminating the unstable axial magnetic force, but the efficiency of such designs may be lower and the magnetic flux density in the immediate vicinity of the pump may violate safety standards and produce some tissue heating. In any case, the stiffness is acceptably small for slotless windings with the yokes present. Another alternative would be to insert the windings in slots in laminated iron stators which would increase motor efficiency and enable use of less magnet material and potentially lighter impeller blades. However, the unstable magnetic forces would be significant for such slotted motors. Also, the necessity for fat blades to generate the required bearing forces in this embodiment allows room for large magnets, and so slotless windings are chosen in the preferred embodiment.

Instead of determining the yoke positions so that the impeller has zero magnetic axial force in the central position, it may be possible to provide a bias axial magnetic force on the impeller, which can counteract other forces such as any average bulk hydrodynamic axial force. In particular, by ensuring a net axial force into the conical body, the thrust bearings on the cover surface can be made superfluous. However, such a bias would demand greater average thrust forces, smaller gaps and increased blood damage, and so the recommended goal is to zero both the magnetic and bulk hydrodynamic axial forces on the impeller when centrally positioned.

The overall design requirement for exclusive hydrodynamic suspension requires control of the external force balance to make the relative magnitude of hydrodynamic thrust sufficient to overcome the external forces. Typical external forces include gravitational forces and net magnetic forces arising as a result of the motor drive.

There are many options for the winding topology and number of phases. FIG. 5A depicts the preferred topology for the body winding 15, viewed from the inlet axis.

The cover winding 16 looks similar but the coils need not avoid the inlet tube and so they appear more triangular in shape. The body winding has a more complex three-dimensional shape with bends at the ends of the body cone section. Each winding consists of three coils. Each coil is made from a number of turns of an insulated conductor such as copper with the number of turns chosen to suit the desired voltage. The coil side mid-lines span an angle of about 50°–100° at the axis when the coils are in position. The coils for body and cover are aligned axially and the axially adjacent coils are connected in either parallel or series connection to form one phase of the three phase winding. Parallel connection offers one means of redundancy in that if one coil fails, the phase can still carry current through the other coil. In parallel connection each of the coil and body winding has a neutral point connection as depicted in FIG. 5A, whereas in series connection, only one of the windings has a neutral point.

Figure 5B:
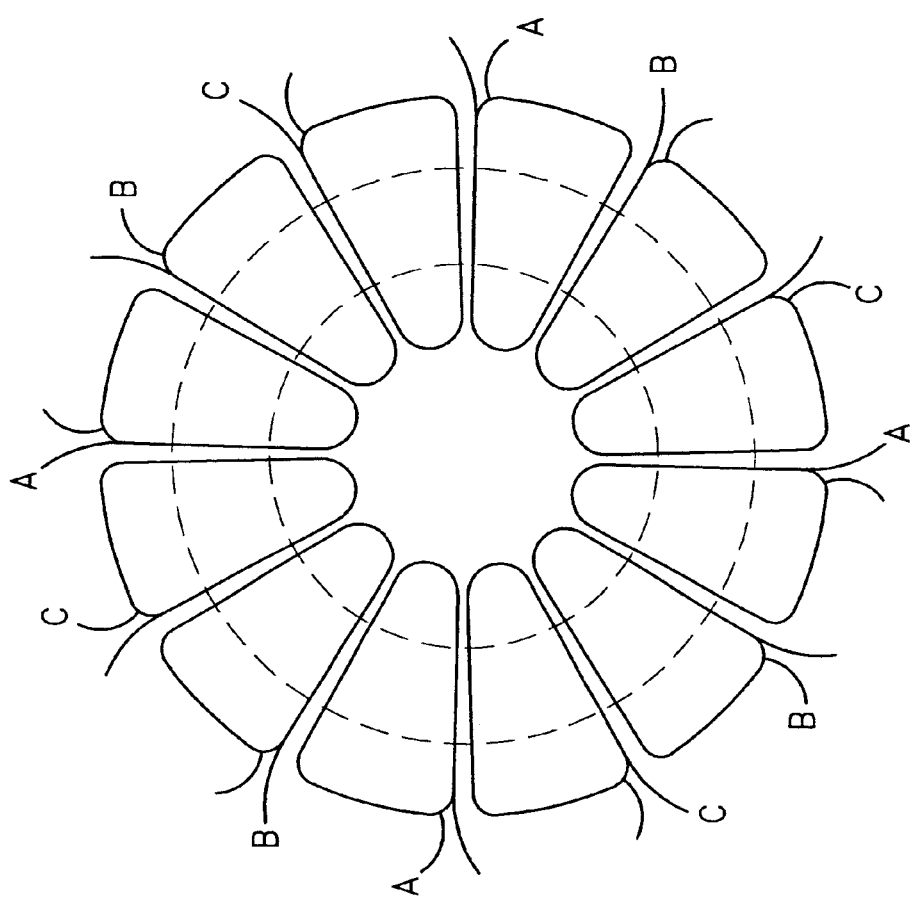
FIGS. 5A, B and C are left-hand end views of possible winding geometries taken generally along the line S—S of FIG. 1.

An alternative three phase winding topology, depicted in FIG. 5B, uses four coils per phase for each of the body and cover windings, with each coil wrapping around the yoke, a topology called a "Gramm ring" winding.

Figure 5C:
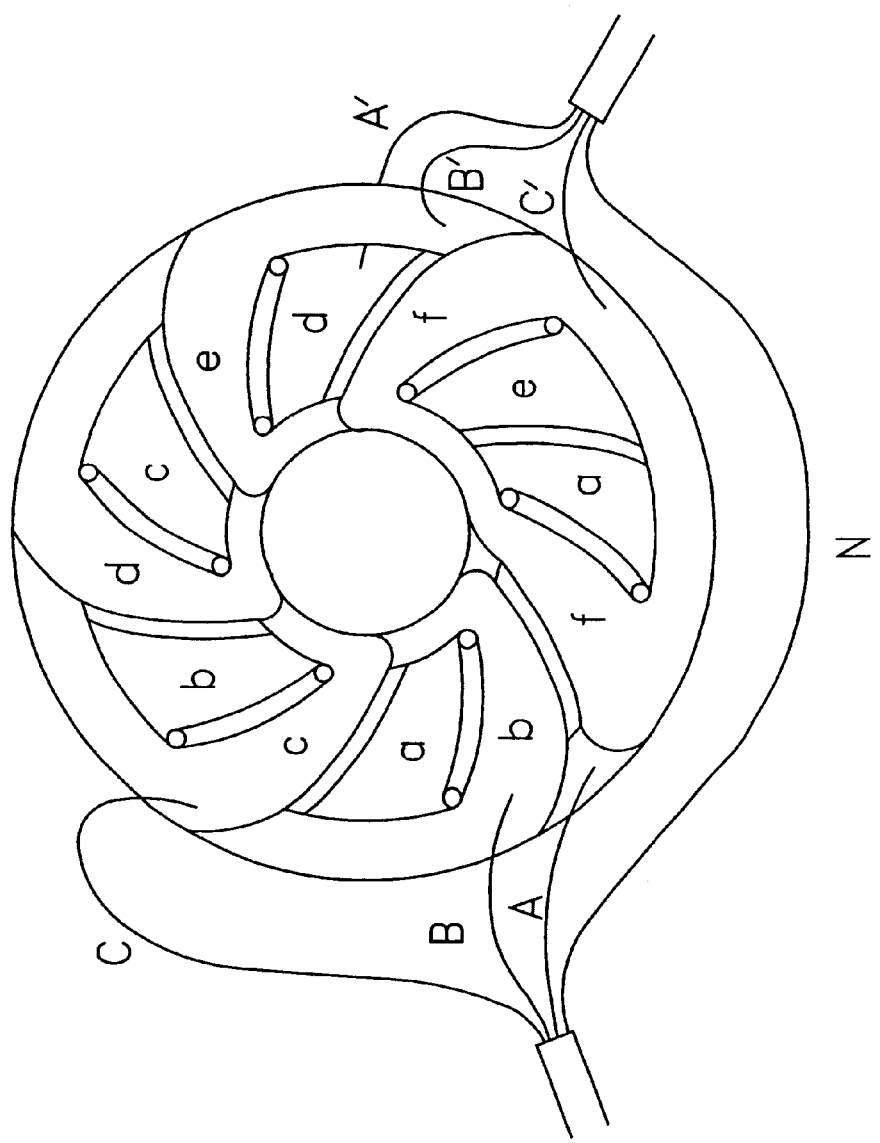

Yet another three phase winding topology, depicted in FIG. 5C, uses two coils per phase for each of the body and cover windings, and connects the coil sides by azimuthal end-windings as is standard motor winding practice. The coils are shown tilted to approximately follow the blade curvature, which can increase motor efficiency, especially for the phase energising strategy to be described below in which only one phase is energised at a time. The winding construction can be simplified by laying the coils around pins protruding from a temporary former, the pins shown as dots in 2 rings of 6 pins each in FIG. 5C. The coils are labelled alphabetically in the order in which they would be layed, coils a and d for phase A, b and e for phase B, and c and f for phase C. Instead of or as well as pins, the coil locations could be defined by thin fins, running between the pins in FIG. 5C, along the boundary between the coils. The coil connections depicted in FIG. 5C are those appropriate for the winding nearest the motor terminals for the case of series connection, with the optional lead from the neutral point on the other winding included.

The winding topologies depicted in FIGS. 5B and C allow the possibility of higher motor efficiency but only if significantly higher coil mass is allowed, and since option FIG. 5A is more compact and simpler to manufacture, it is the preferred option. Material ribs between the coils of option FIG. 5A can be used to stiffen the housing.

Multi-stranded flexible conductors within a suitable bio-compatible cable can be used to connect the motor windings to a motor controller. The energisation of the three phases can be performed by a standard sensorless controller, in which two out of six semiconducting switches in a three phase bridge are turned on at any one time. Alternatively, because of the relatively small fraction of the impeller cross-section occupied by magnets, it may be slightly more efficient to only activate one of the three phases at a time, and to return the current by a conductor from the neutral point in the motor. Careful attention must be paid to ensure that the integrity of all conductors and connections is failsafe.

In the preferred embodiment, the two housing components 3 and 4 are made by injection moulding from non-electrically conducting plastic materials such as Lexan polycarbonate plastic. Alternatively the housing components can be made from ceramics. The windings and yokes are ideally encapsulated within the housing during fabrication moulding. In this way, the separation between the winding and the magnets is minimised, increasing the motor efficiency, and the housing is thick, increasing its mechanical stiffness. Alternatively, the windings can be positioned outside the housing, of thickness at least around 2 mm for sufficient stiffness.

If the housing material plastic is hygroscopic or if the windings are outside the housing, it may be necessary to first enclose the windings and yoke in a very thin impermeable shell. Ideally the shell should be non-conducting (such as ceramic or plastic), but titanium of around 0.1 mm to 0.2 mm thickness would give sufficiently low eddy losses. Encapsulation within such a shell would be needed to prevent winding movement.

Alternatively, the housing components 3 and 4 may be made from a biocompatible metallic material of low electrical conductivity, such as Ti-6Al-4V. To minimise the eddy current loss, the material must be as thin as possible, e.g. 0.1 mm to 0.5 mm, wherever the material experiences high alternating magnetic flux densities, such as between the coils and the housing inner surfaces 10 and 11.

The combining of the motor and bearing components into the impeller in the preferred embodiment provides several key advantages. The rotor consequently has very simple form, with the only cost of the bearing being tight manufacturing tolerances. The rotor mass is very low, minimising the bearing force needed to overcome weight. Also, with the bearings and the motor in the same region of the rotor, the bearings forces are smaller than if they had to provide a torque to support magnets at an extremity of the rotor.

A disadvantage of the combination of functions in the impeller is that its design is a coupled problem. The optimisation should ideally link the fluid dynamics, magnetics and bearing thrust calculations. In reality, the blade thickness can be first roughly sized to give adequate motor efficiency and sufficient bearing forces with a safety margin. Fortuitously, both requirements are met for four blades of approximate average circumferential thickness 6 mm or more. The housing, blade, and support cone shapes can then be designed using computational fluid dynamics, maintaining the above minimum average blade thickness. Finally the motor stator, i.e. winding and yoke, can be optimised for maximum motor efficiency.

Figure 6:
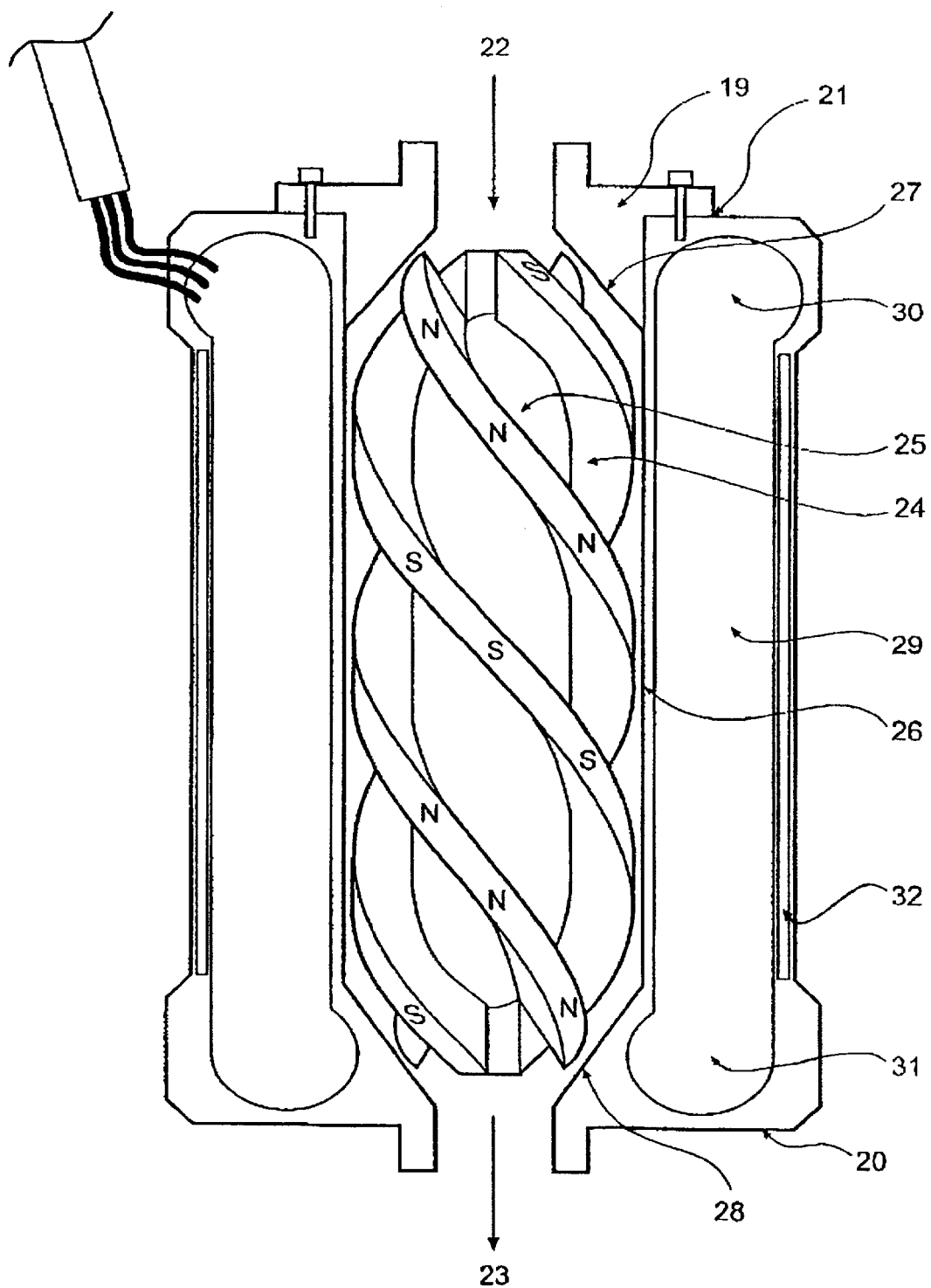
FIG. 6 is a diagrammatic cross-sectional view of an alternative embodiment of the invention as an axial pump.

FIG. 6 depicts an alternative embodiment of the invention as an axial pump. The pump housing is made of two parts, a front part 19 and a back part 20, joined for example at 21. The pump has an axial inlet 22 and axial outlet 23. The impeller comprises only blades 24 mounted on a support cylinder 25 of reducing radius at each end. An important feature of this embodiment is that the blade edges are tapered to generate hydrodynamic thrust forces which suspend the impeller. These forces could be used for radial suspension alone from the straight section 26 of the housing, with some alternative means used for axial suspension, such as stable axial magnetic forces or a conventional tapered-land type hydrodynamic thrust bearing. FIG. 6 proposes a design which uses the tapered blade edges to also provide an axial hydrodynamic bearing. The housing is made with a reducing radius at its ends to form a front face 27 and a back face 28 from which the axial thrusts can suspend the motor axially. Magnets are embedded in the blades with blades having alternating polarity and four blades being recommended. Iron in the outer radius of the support cylinder 25 can be used to increase the magnet flux density. Alternatively, the magnets could be housed in the support cylinder and iron could be used in the blades. A slotless helical winding 29 is recommended, with outward bending end-windings 30 at one end to enable insertion of the impeller and inward bending windings 31 at the other end to enable insertion of the winding into a cylindrical magnetic yoke 32. The winding can be encapsulated in the back housing part 20.

THIRD EMBODIMENT

With reference to FIGS. 7 to 15 inclusive there is shown a further preferred embodiment of the pump assembly 200.

Figure 7:
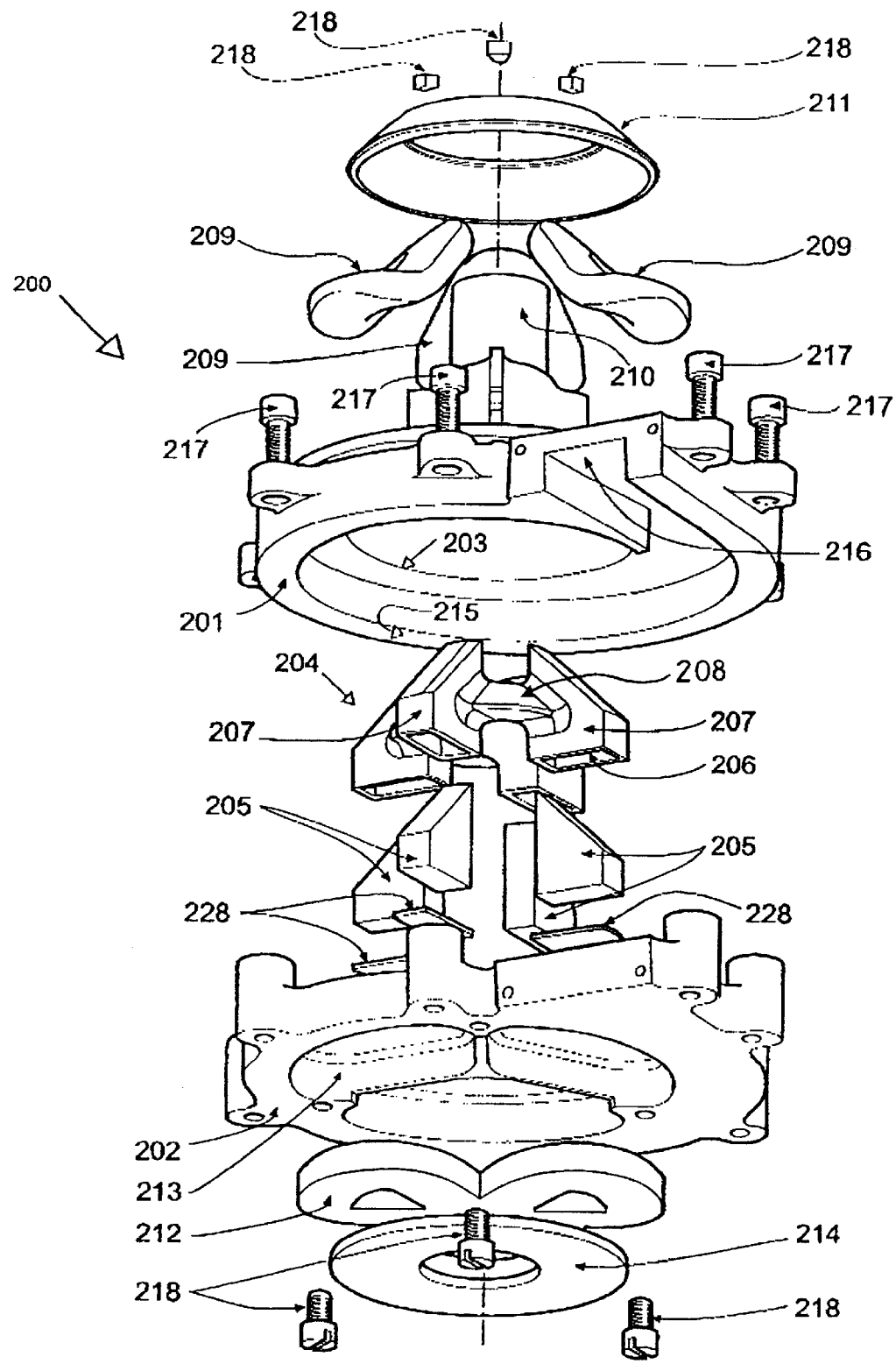
FIG. 7 is an exploded, perspective view of a centrifugal pump assembly according to a further embodiment of the invention.

With particular reference initially to FIG. 7 the pump assembly 200 comprises a housing body 201 adapted for bolted connection to a housing cover 202 and so as to define a centrifugal pump cavity 203 therewithin.

The cavity 203 houses an impeller 204 adapted to receive magnets 205 within cavities 206 defined within blades 207. As for the first embodiment the blades 207 are supported from a support cone 208.

Exterior to the cavity 203 but forming part of the pump assembly 200 there is located a body winding 209 symmetrically mounted around inlet 210 and housed between the housing body 201 and a body yoke 211.

Also forming part of the pump assembly 200 and also mounted external to pump cavity 203 is cover winding 212 located within winding cavity 213 which, in turn, is located within housing cover 202 and closed by cover yoke 214.

Figure 12:
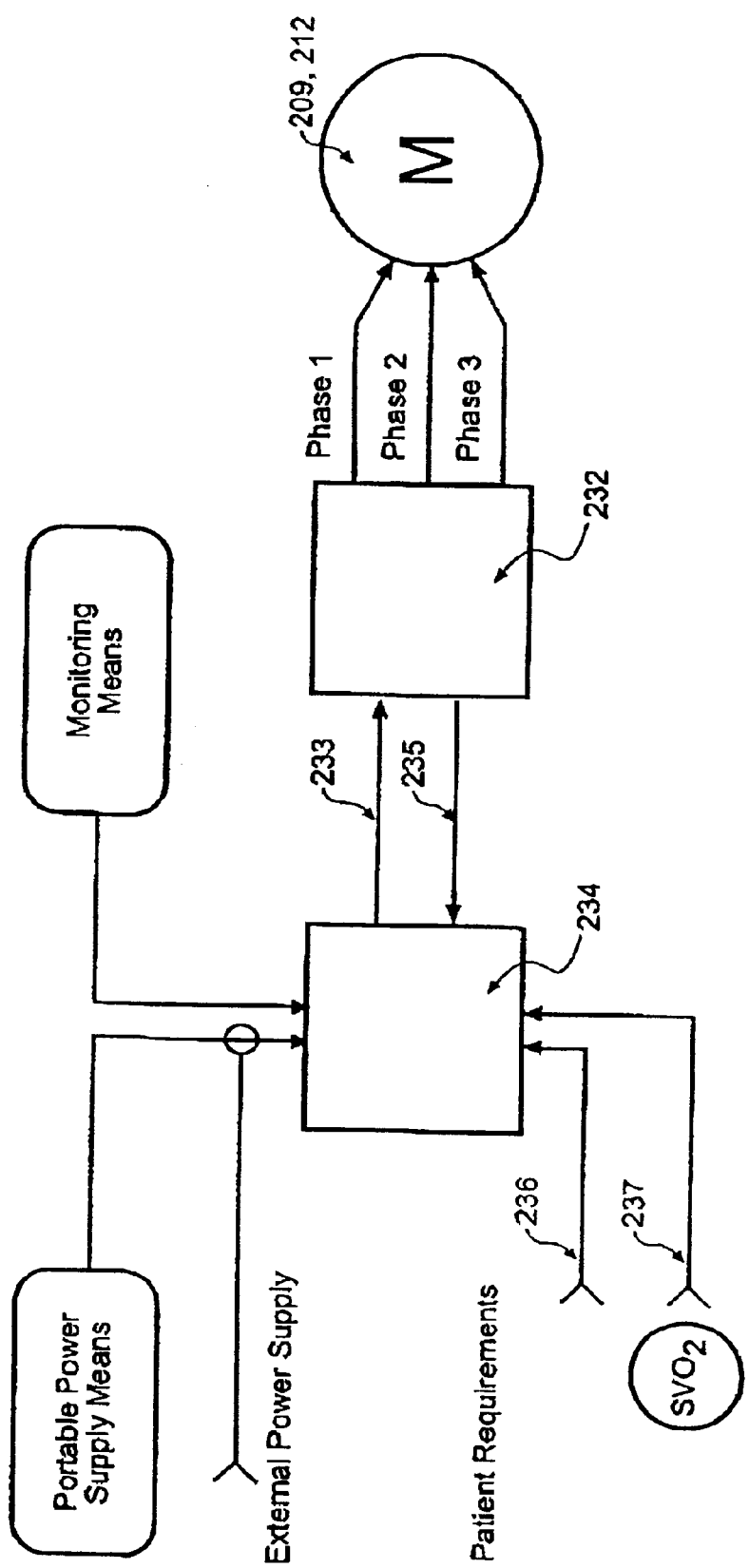
FIG. 12 is a block diagram of an electronic driver circuit for the pump assembly of FIG. 7.

The windings 212 and 209 are supplied from the electronic controller of FIG. 12 as for the first embodiment the windings are arranged to receive a three phase electrical supply and so as to set up a rotating magnetic field within cavity 203 which exerts a torque on magnets 205 within the impeller 204 so as to urge the impeller 204 to rotate substantially about central axis TT of cavity 203 and in line with the longitudinal axis of inlet 210. The impeller 204 is caused to rotate so as to urge fluid (in this case blood) around volute 215 and through outlet 216.

The assembly is bolted together in the manner indicated by screws 217. The yokes 211, 214 are held in place by fasteners 218. Alternatively, press fitting is possible provided sufficient integrity of seal can be maintained.

Figure 8:
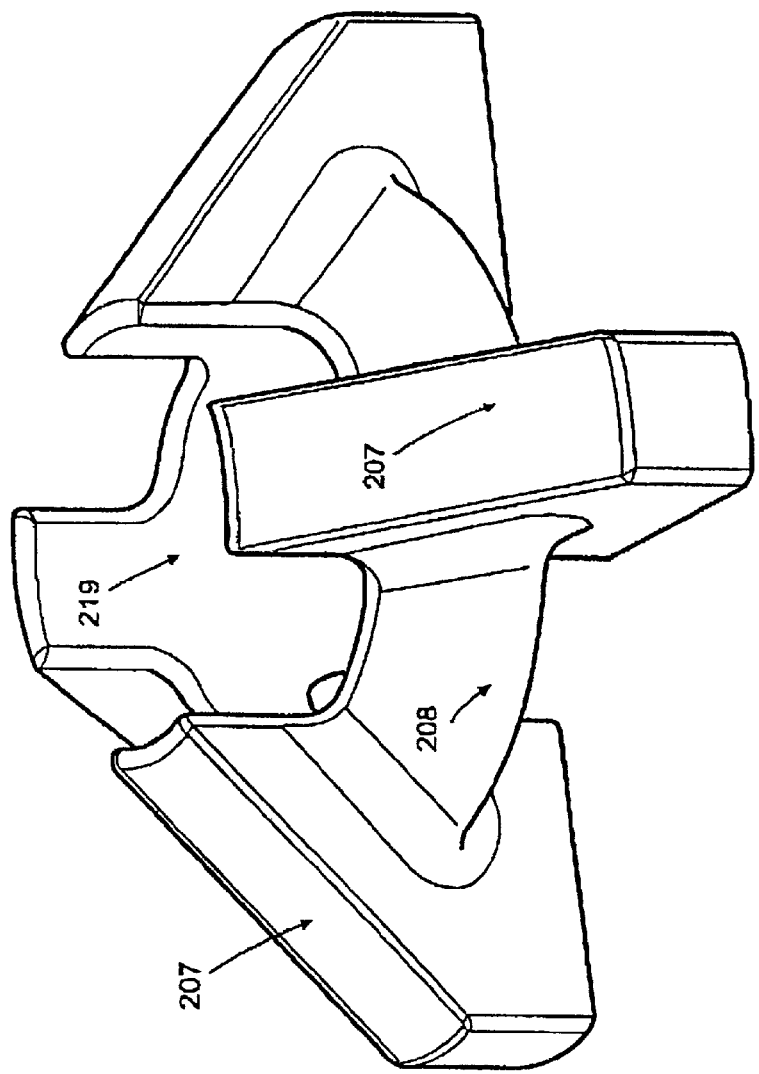
FIG. 8 is a perspective view of the impeller of the assembly of FIG. 7.

FIG. 8 shows the impeller 204 of this embodiment and clearly shows the support cone 208 from which the blades 207 extend. The axial cavity 219 which is arranged, in use, to be aligned with the longitudinal axis of inlet 210 and through which blood is received for urging by blades 207 is clearly visible.

Figure 9:
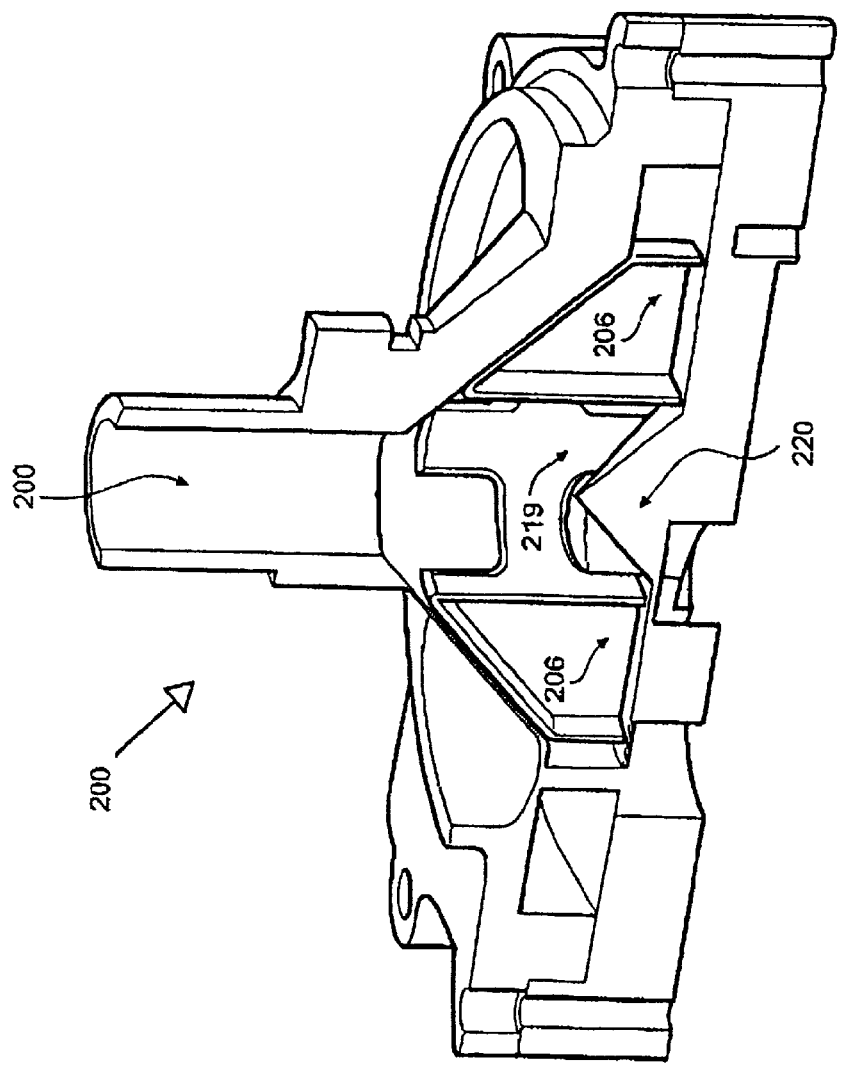
FIG. 9 is a perspective, cut away view of the impeller of FIG. 8 within the pump assembly of FIG. 7.

The cutaway view of FIG. 9 shows the axial cavity 219 and also the magnet cavities 206 located within each blade 207. The preferred cone structure 220 extending from housing cover 202 aligned with the axis of inlet 210 and axial cavity 219 of impeller 204 is also shown.

Figure 10:
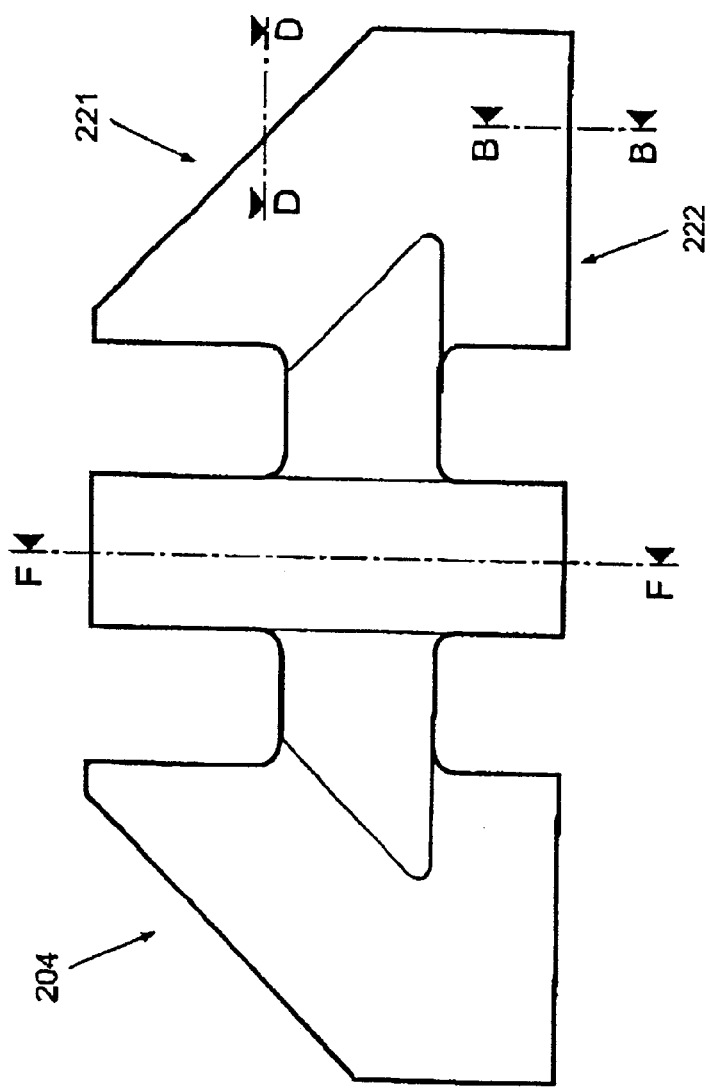
FIG. 10 is a side section indicative view of the impeller of FIG. 8.

FIG. 10 is a side section, indicative view of the impeller 204 defining the orientations of central axis FF, top taper edge DD and bottom taper edge BB, which tapers are illustrated in FIG. 11 in side section view.

Figure 11A:
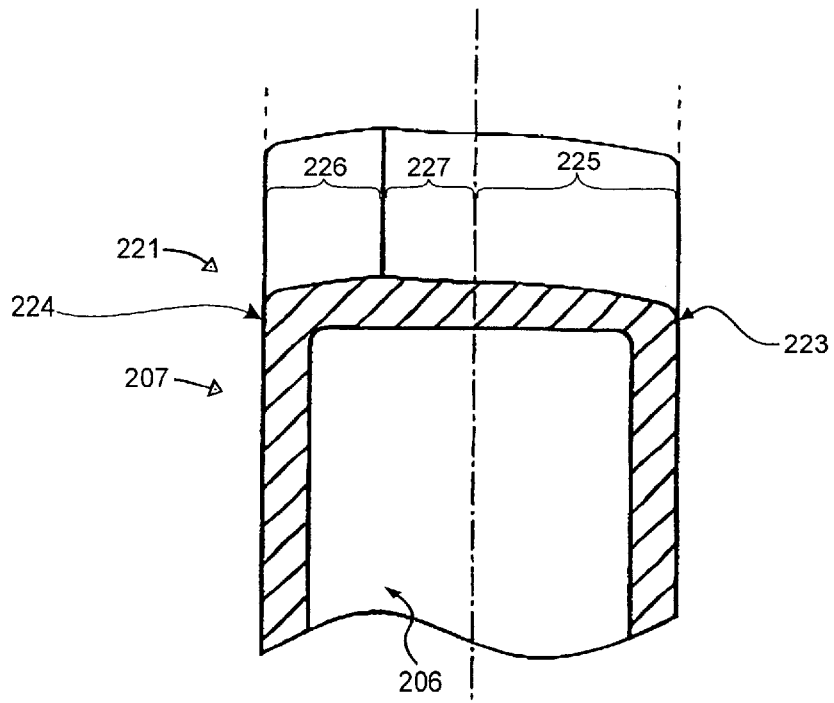
FIG. 11 is a detailed view in side section of edge portions of the impeller of FIG. 10.

FIG. 11A is a section of a blade 207 of impeller 204 taken through plane DD as defined in FIG. 10 and shows the top edge 221 to be profiled from a leading edge 223 to a trailing edge 224 as follows: central portion 227 comprises an ellipse with centre on the dashed midline having a semi-major axis of radius 113 mm and a semi-minor axis of radius 80 mm and then followed by leading conical surface 225 and trailing conical surface 226 on either side thereof as illustrated in FIG. 11A. The leading surface 225 has radius 0.05 mm less than the trailing surface 226. This prescription is for a taper which can be achieved by a grinding wheel, but many alternative prescriptions could be devised to give a taper of similar utility.

The leading edge 223 is radiused as illustrated.

Figure 11B:
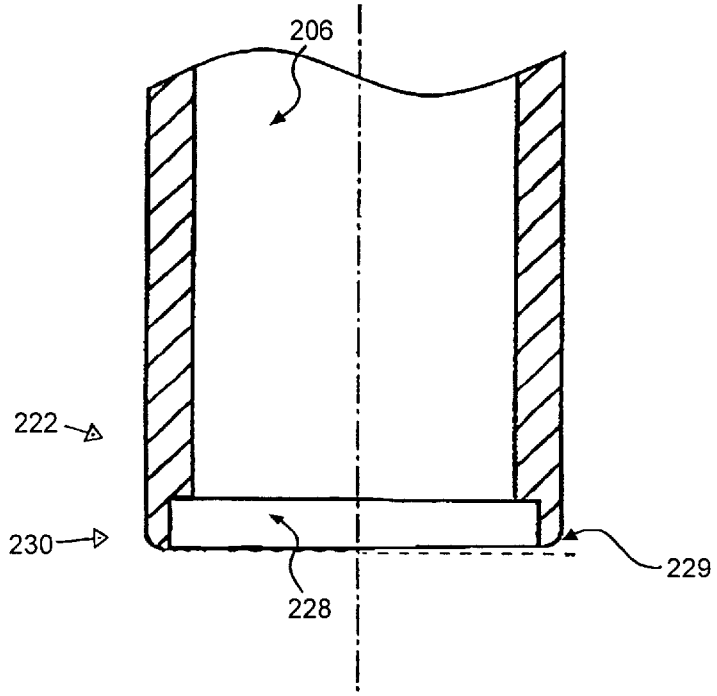

FIG. 11B illustrates in cross-section the bottom edge 222 of blade 207 cut along plane BB of FIG. 10.

The bottom edge includes cap 228 utilised for sealing magnet 205 within cavity 206.

In this instance substantially the entire edge comprises a straight taper with a radius of 0.05 mm at leading edge 229 and a radius of 0.25 mm at trailing edge 230.

The blade 207 is 6.0 mm in width excluding the radii at either end.

FIG. 12 comprises a block diagram of the electrical controller suitable for driving the pump assembly 200 and comprises a three phase commutation controller 232 adapted to drive the windings 209, 212 of the pump assembly. The commutation controller 232 determines relative phase and frequency values for driving the windings with reference to set point speed input 233 derived from physiological controller 234 which, in turn, receives control inputs 235 comprising motor current input and motor speed (derived from the commutation controller 232), patient blood flow 236, and venous oxygen saturation 237. The pump blood flow can be approximately inferred from the motor speed and current via curve-fitted formulae.

Figure 13:
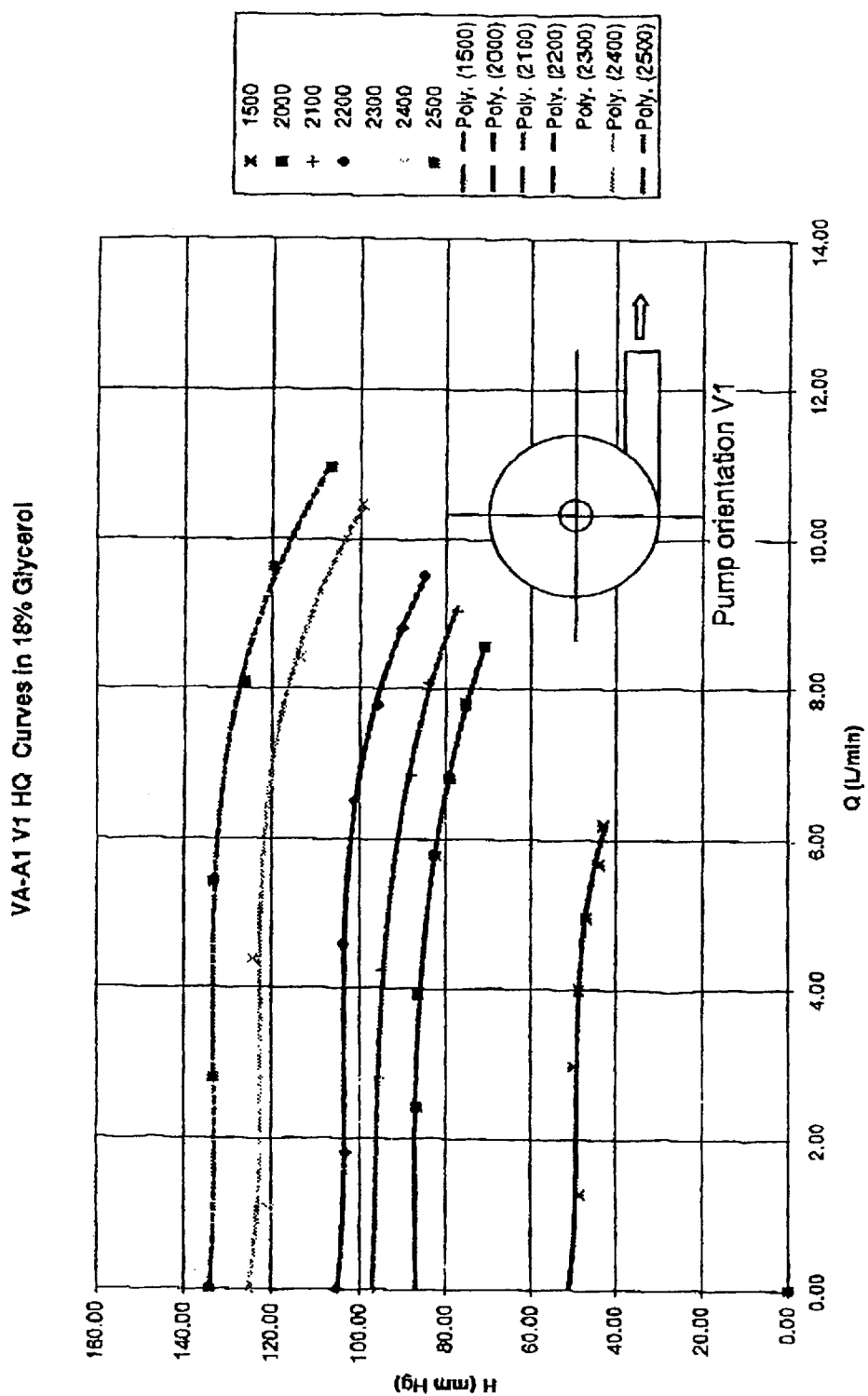
FIG. 13 is a graph of head versus flow for the pump assembly of FIG. 7.

FIG. 13 is a graph of pressure against flow for the pump assembly 200 where the fluid pumped is 18% glycerol for impeller rotation velocity over the range 1500 RPM to 2500 RPM. The 18% glycerol liquid is believed to be a good analogue for blood under certain circumstances, for example in the housing gap.

Figure 14:
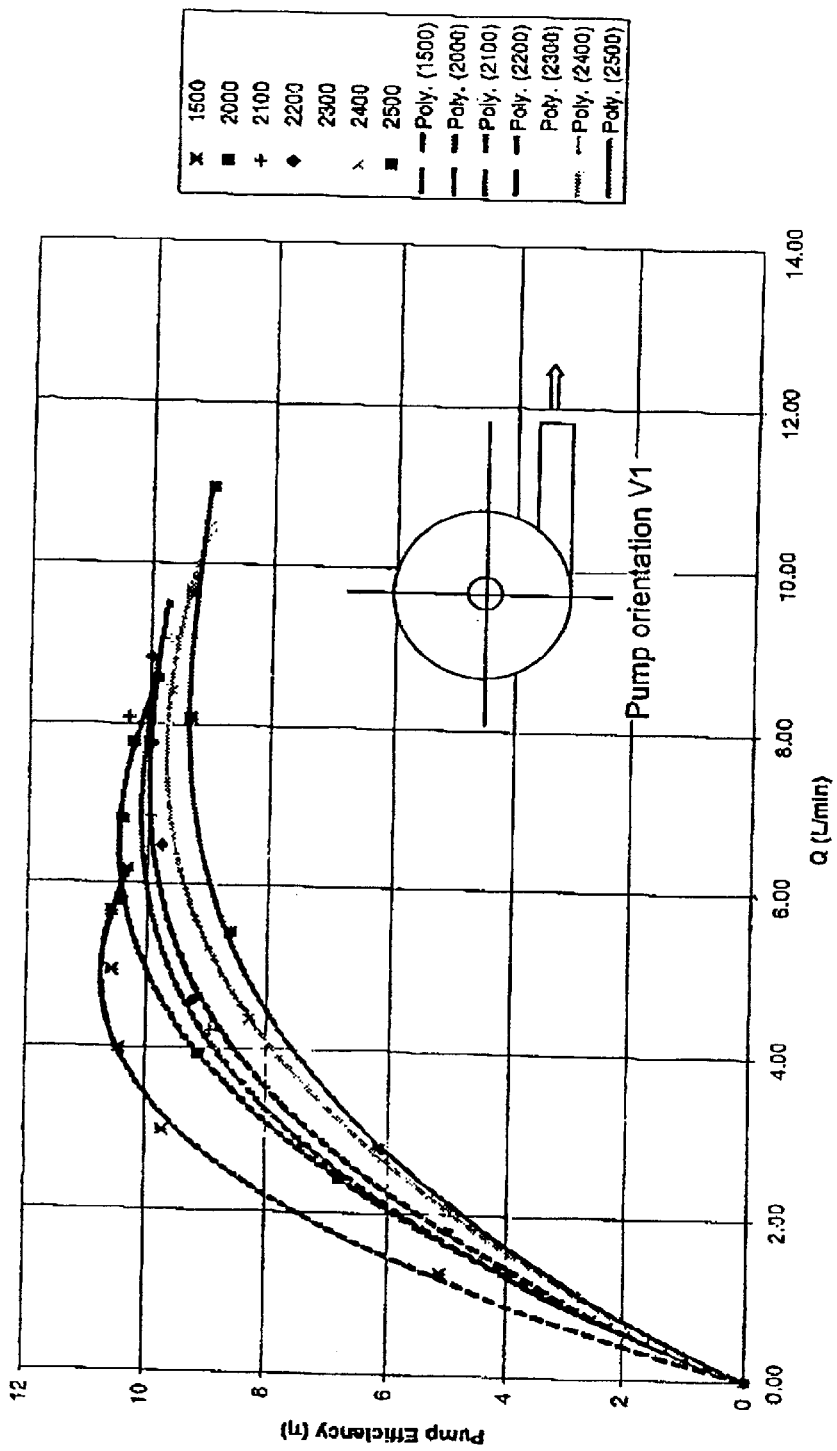
FIG. 14 is a graph of pump efficiency versus flow for the pump assembly of FIG. 7.

FIG. 14 graphs pump efficiency against flow for the same fluid over the same speed ranges as for FIG. 13.

Figure 15:
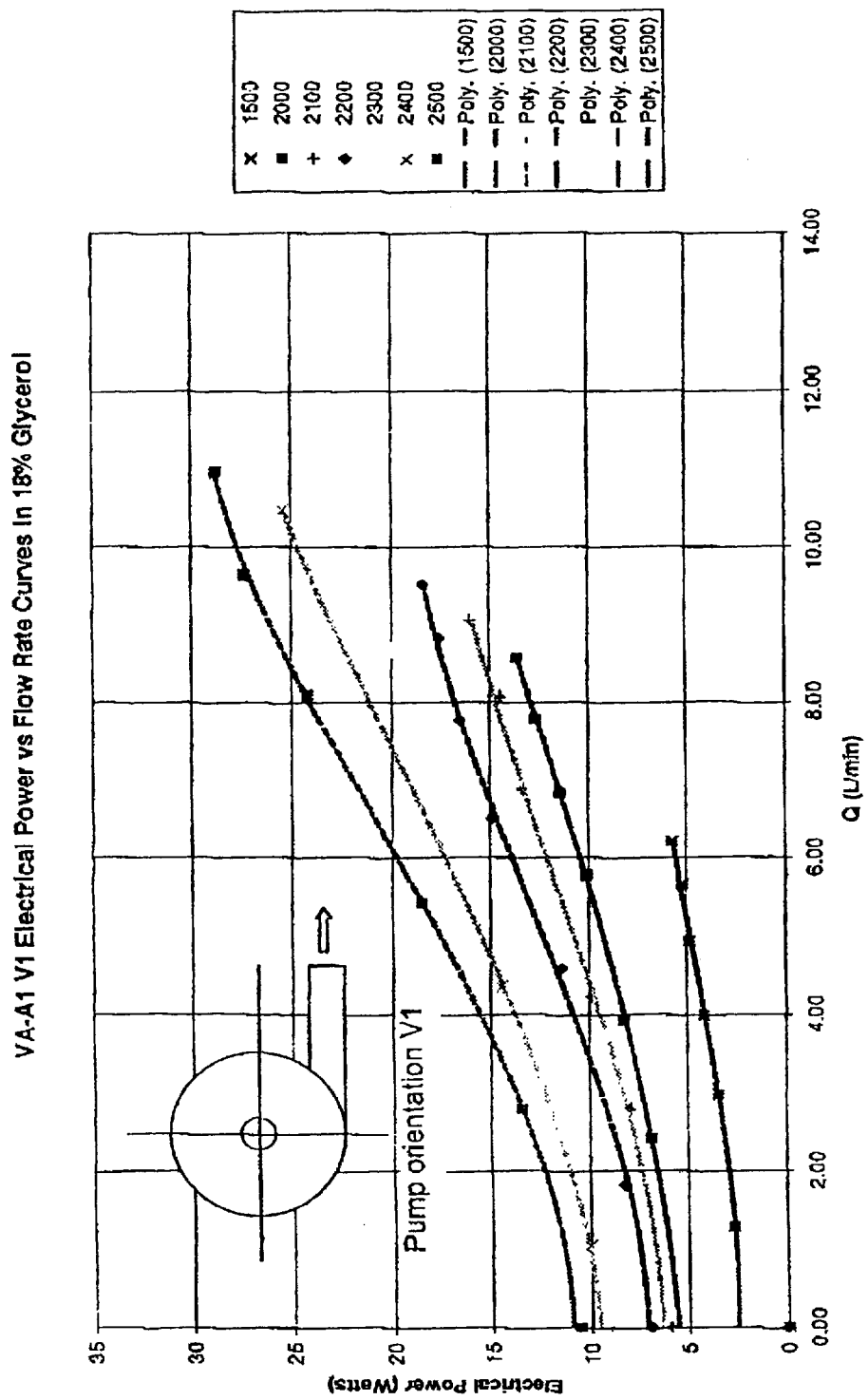
FIG. 15 is a graph of electrical power consumption versus flow for the pump assembly of FIG. 7.
Figure 16:
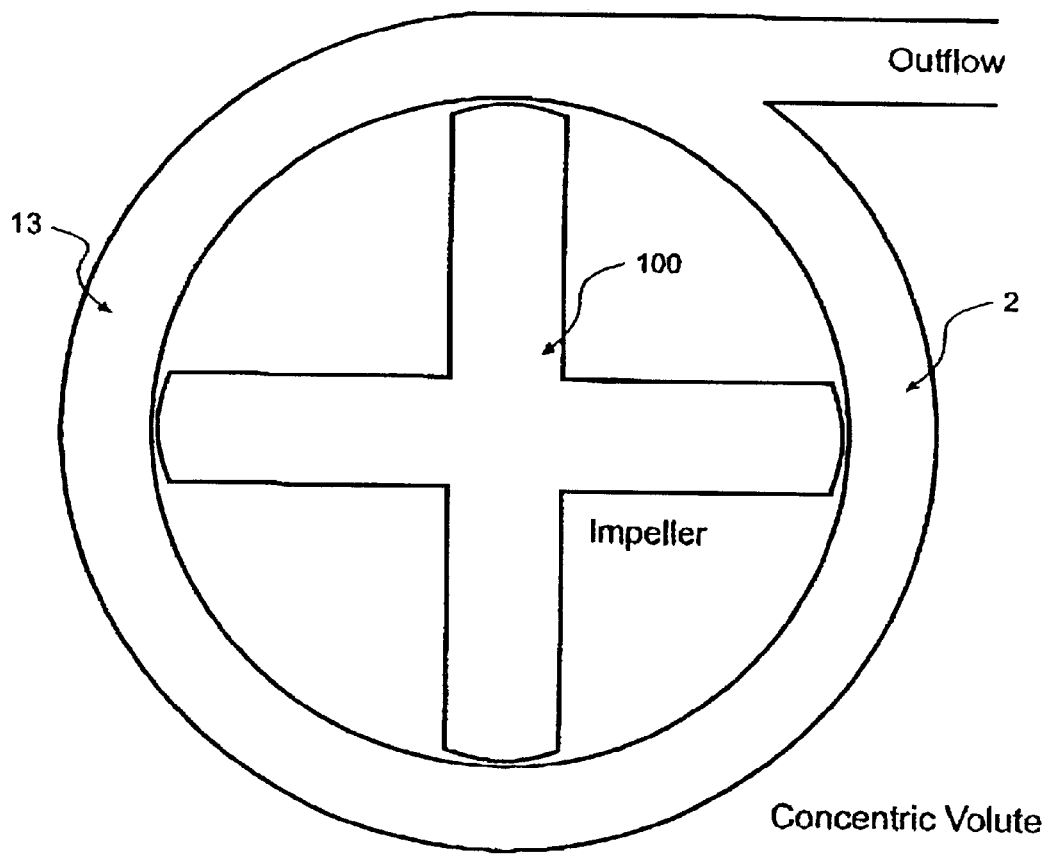
FIG. 16 is a plan, section view of the pump assembly showing a volute arrangement according to a preferred embodiment.

FIG. 15 is a graph of electrical power consumption against flow for the same fluid over the same speed ranges as for FIG. 13.

The common theme running through the first, second and third embodiments described thus far is the inclusion in the impeller of a taper or other deformed surface which, in use, moves relative to the adjacent housing wall thereby to cause a restriction with respect to the line of movement of the taper or deformity thereby to generate thrust upon the impeller which includes a component substantially normal to the line of movement of the surface and also normal to the adjacent internal pump wall with respect to which the restriction is defined for fluid located therebetween.

In order to provide both radial and axial direction control at least one set of surfaces must be angled with respect to the longitudinal axis of the impeller (preferably at approximately 45° thereto) thereby to generate or resolve opposed radial forces and an axial force which can be balanced by a corresponding axial force generated by at least one other tapered or deformed surface located elsewhere on the impeller.

In the forms thus far described top surfaces of the blades 8, 207 are angled at approximately 45° with respect to the longitudinal axis of the impeller 100, 204 and arranged for rotation with respect to the internal walls of a similarly angled conical pump housing. The top surfaces of the blades are deformed so as to create the necessary restriction in the gap between the top surfaces of the blades and the internal walls of the conical pump housing thereby to generate a thrust which can be resolved to both radial and axial components.

In the examples thus far the bottom faces of the blades 8, 207 comprise surfaces substantially lying in a plane at right angles to the axis of rotation of the impeller and, with their deformities define a gap with respect to a lower inside face of the pump housing against which a substantially only axial thrust is generated.

Other arrangements are possible which will also, relying on these principles, provide the necessary balanced radial and axial forces. Such arrangements can include a double cone arrangement where the conical top surface of the blades is mirrored in a corresponding bottom conical surface. The only concern with this arrangement is the increased depth of pump which can be a problem for in vivo applications where size minimisation is an important criteria.

FOURTH EMBODIMENT

Figure 18:
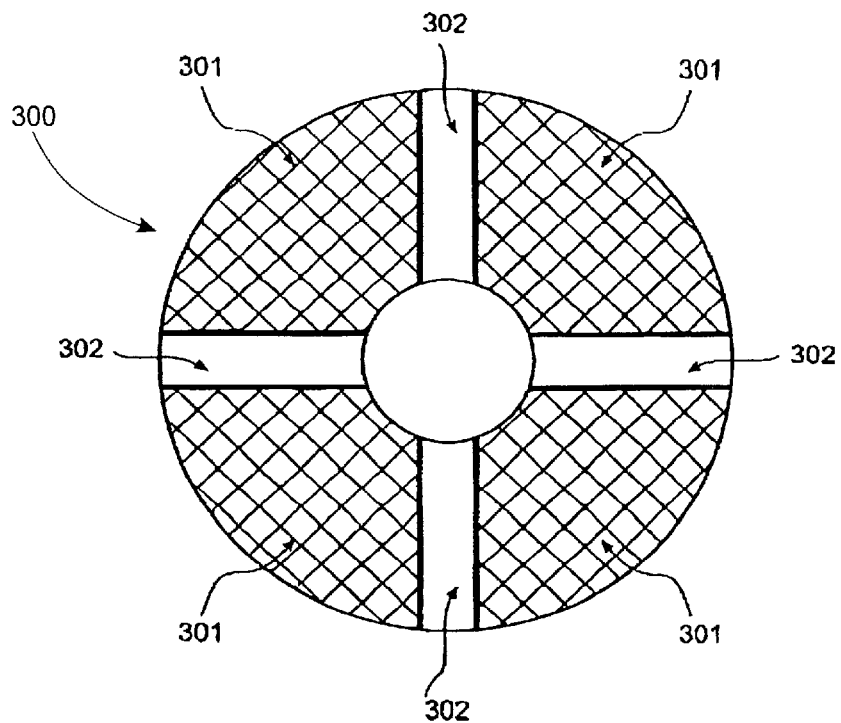
FIG. 18 is a plan view of an impeller according to a further embodiment of the invention.

With reference to FIG. 18 a further embodiment of the invention is illustrated comprising a plan view of the impeller 300 forming part of a "channel" pump. In this embodiment the blades 301 have been widened relative to the blades 207 of the third embodiment to the point where they are almost sector-shaped and the flow gaps between adjacent blades 301, as a result, take the form of a channel 302, all in communication with axial cavity 303.

Figure 19:
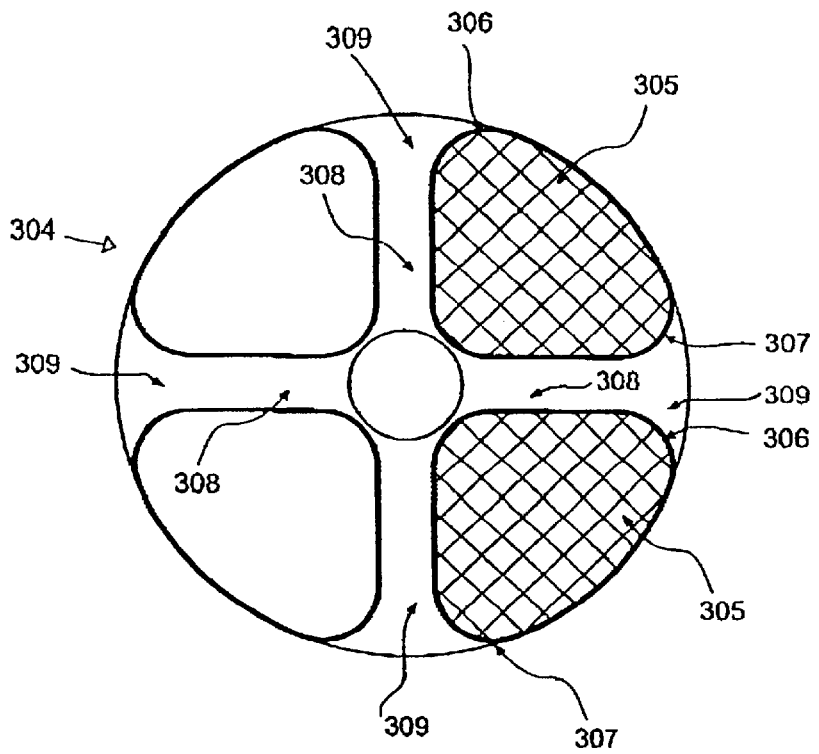
FIG. 19 is a plan view of an impeller according to a further embodiment of the invention.

A further modification of this arrangement is illustrated in FIG. 19 wherein impeller 304 includes sector-shaped blades 305 having curved leading and trailing portions 306, 307 respectively thereby defining channels 308 having fluted exit portions 309.

As with the first and second embodiments the radial and axial hydrodynamic forces are generated by appropriate profiling of the top and bottom faces of the blades 301, 305 (not shown in FIGS. 18 and 19).

Figure 20:
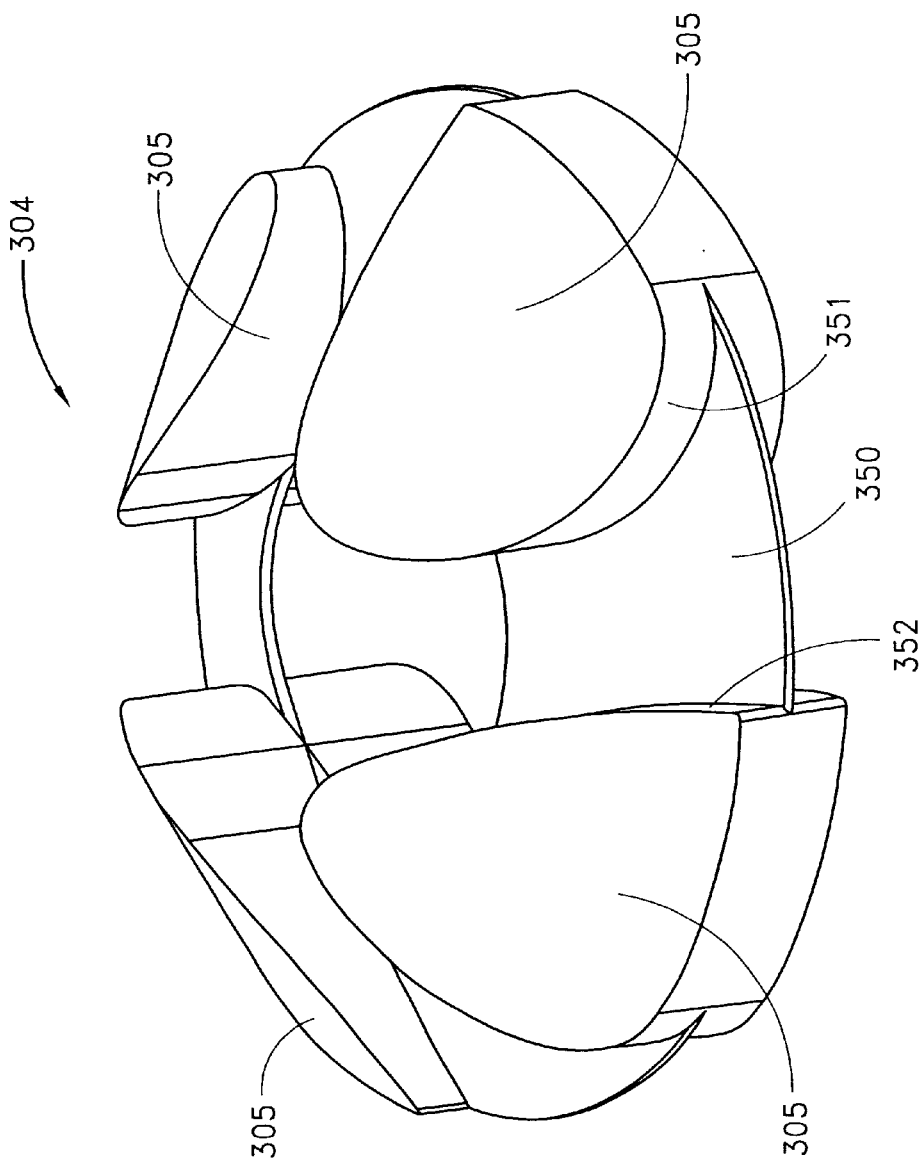
FIG. 20 is a perspective view of an impeller according to a further embodiment of the invention.

FIG. 20 illustrates a perspective view of an impeller 304 which follows the theme of the impeller arrangement of FIGS. 18 and 19 in perspective view and where like parts are numbered as for FIG. 19. In this case the four blades 305 are joined at mid-portions thereof by a blade support in the form of a conical rim 350 and have edge portions which are shaped so as to have an increased curvature on the trailing edge 351 thereof compared with the leading edge 352.

FIFTH EMBODIMENT

Figure 21:
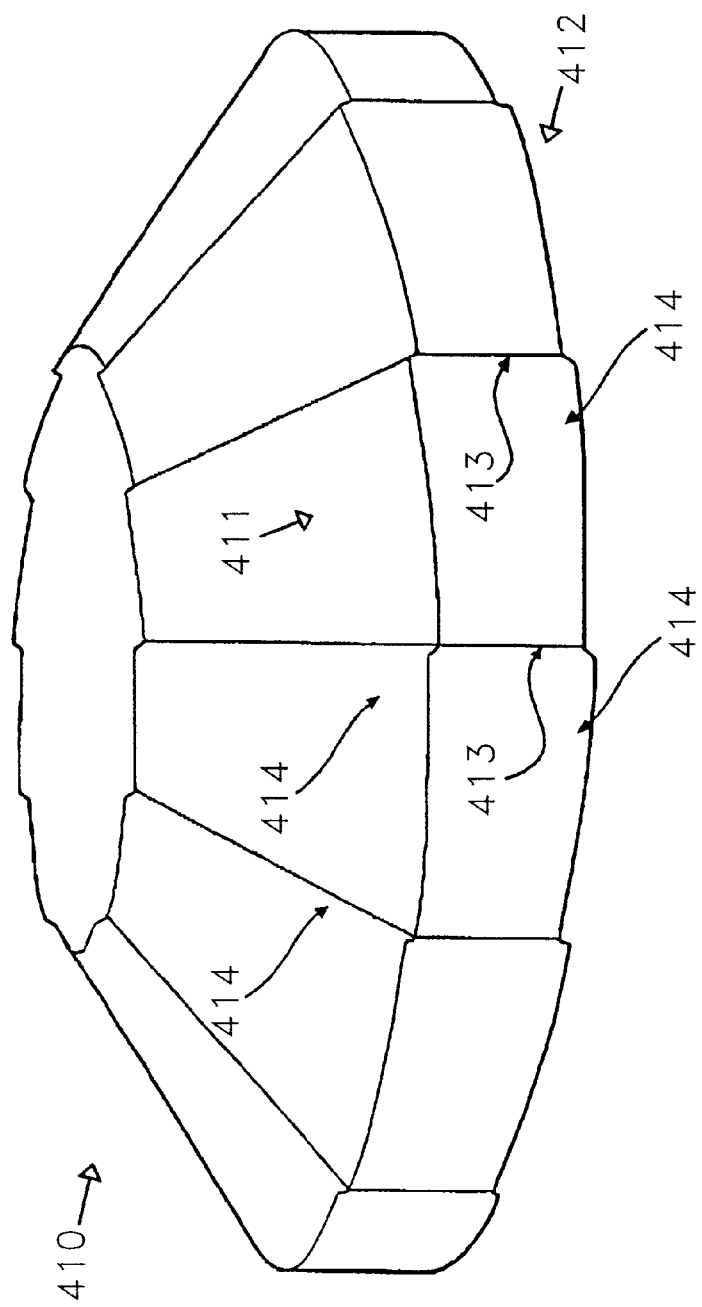
FIG. 21 is a perspective view of an impeller according to yet a further embodiment of the invention.

A fifth embodiment of a pump assembly according to the invention comprises an impeller 410 as illustrated in FIG. 21 where, conceptually, the upper and lower surfaces of the blades of previous embodiments are interconnected by a top shroud 411 and a bottom shroud 412. In this embodiment the blades 413 can be reduced to a very small width as the hydrodynamic behaviour imparted by their surfaces in previous embodiments is now given effect by the profiling of the shrouds 411, 412 which, in this instance, comprises a series of smooth-edged wedges with the leading surface of one wedge directly interconnected to the trailing edge of the next leading wedge 414.

As for previous embodiments the top shroud 411 is of overall conical shape thereby to impart both radial and axial thrust forces whilst the bottom shroud 412 is substantially planar thereby to impart substantially only axial thrust forces.

It is to be understood that, whilst the example of FIG. 21 shows the surfaces of the shroud 411 angled at approximately 45° to the vertical, other inclinations are possible extending to an inclination of 0° to the vertical which is to say the impeller 410 can take the form of a cylinder with surface rippling or other deformations which impart the necessary hydrodynamic lift, in use.

Figure 22:
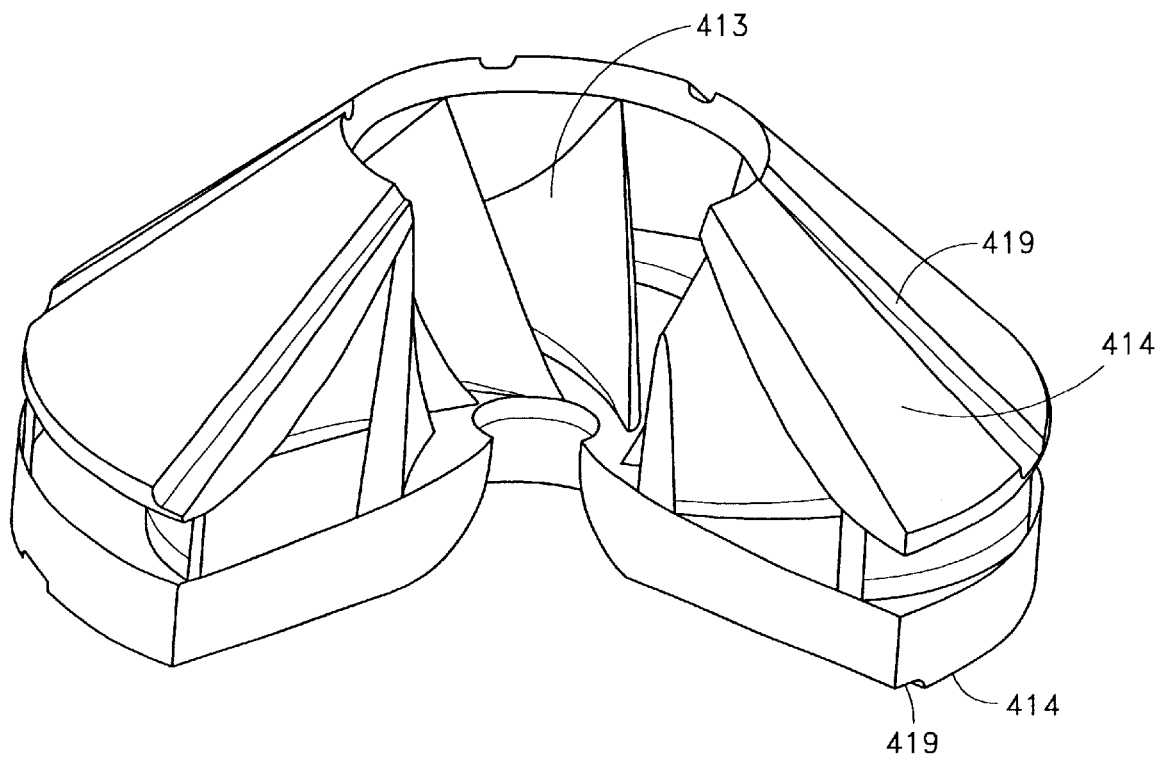
FIG. 22 is a perspective, partially cut away view of an impeller according to yet a further embodiment of the invention.
Figure 23:
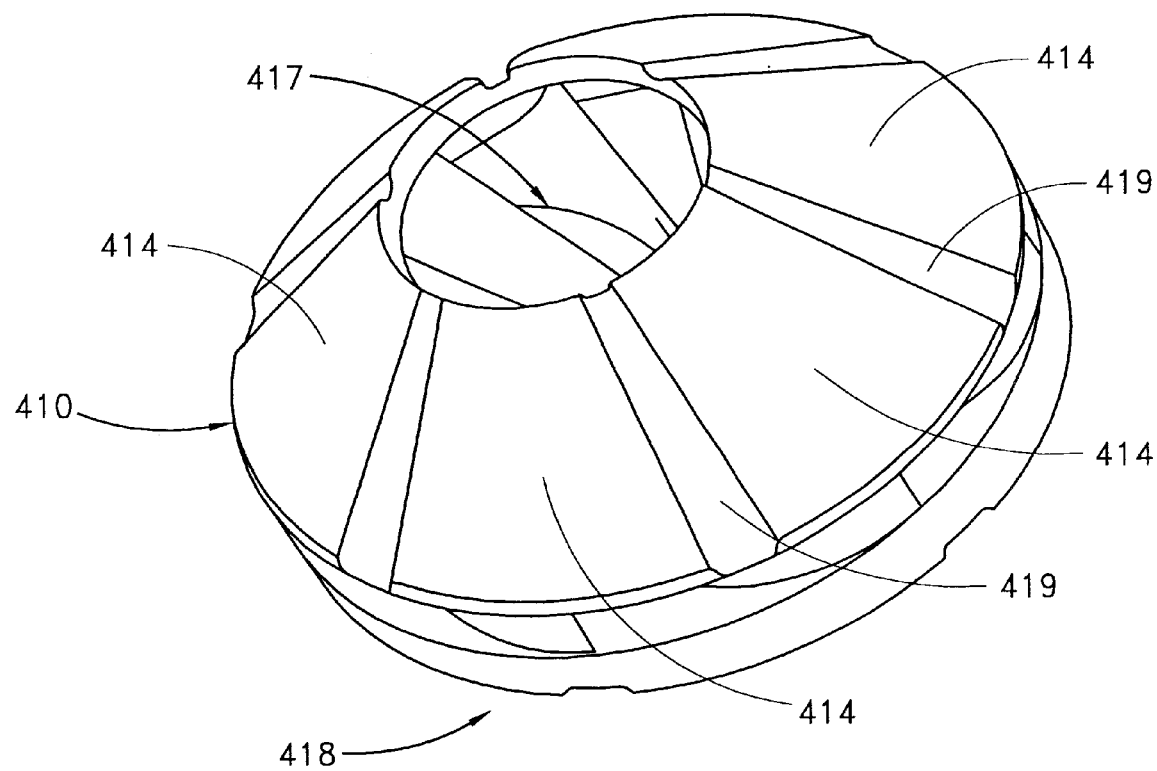
FIG. 23 is a top, perspective view of the impeller of FIG. 22.
Figure 24:
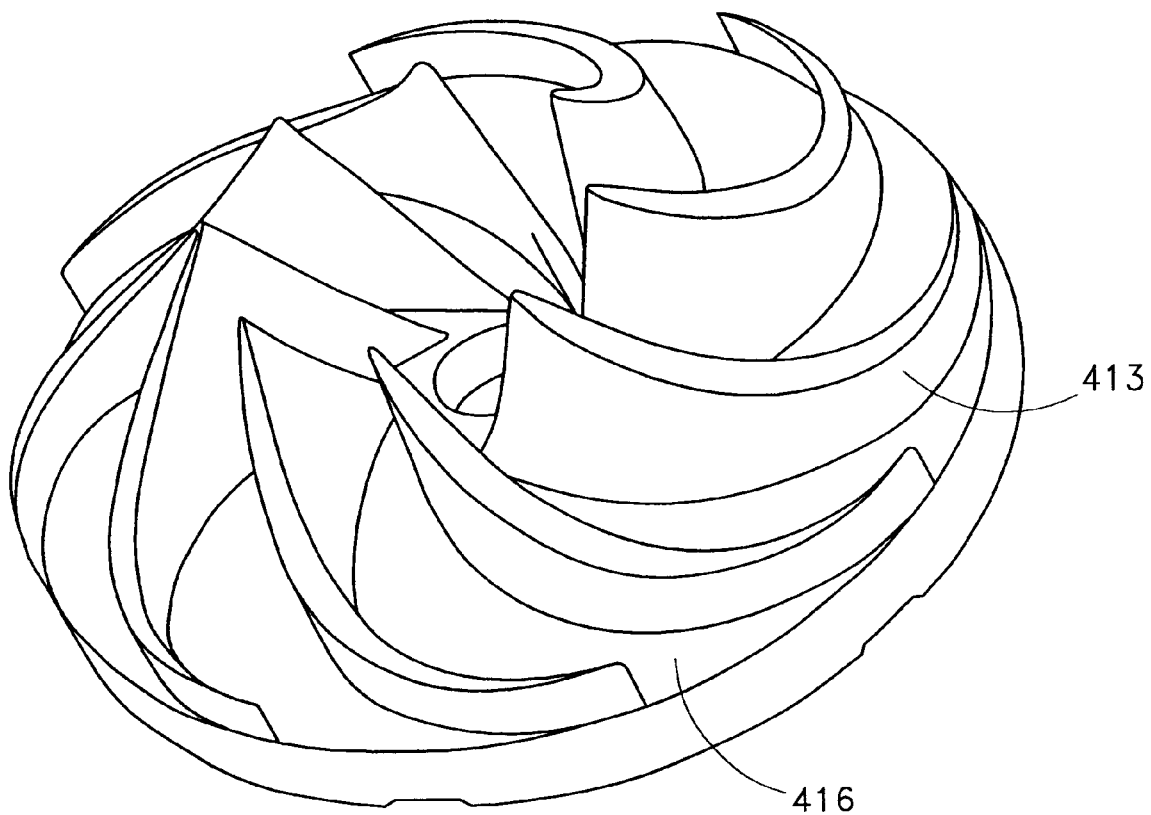
FIG. 24 is a perspective view of the impeller of FIG. 22 with its top shroud removed.

With reference to FIGS. 22 to 24 a specific example of the concept embodied in FIG. 21 is illustrated and wherein like components are numbered as for FIG. 21.

It will be observed that, with reference to FIG. 24, the blades 413 are thin compared to previous embodiments and, in this instance, are arcuate channels 416 therebetween which allow fluid communication from a centre volume 417 to the periphery 418 of the impeller 410.

In this arrangement it will be noted that the wedges 414 are separated one from the other on each shroud by channels 419. The channels extend radially down the shroud from the centre volume 417 to the periphery 418.

In such designs with thin blades, the magnets required for the driving torque can be contained within the top or bottom volute or both, along with the optional soft magnetic yokes to increase motor efficiency.

A variation of this embodiment is to have the wedge profiling cut into the inner surfaces of the housing and have smooth shroud surfaces.

SIXTH EMBODIMENT

Figure 25:
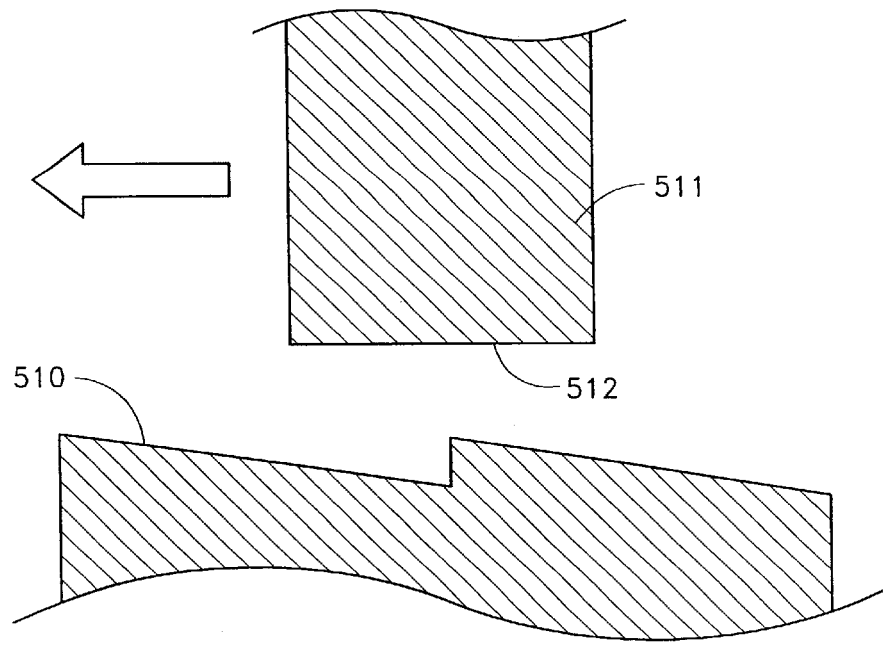
FIG. 25 illustrates an alternative embodiment wherein the deformed surface is located on the pump housing.

In contrast to the embodiments illustrated with respect to FIGS. 3A, 3B and 3C an arrangement is shown in FIG. 25 wherein the "deformed surface" comprises a stepped formation 510 forming part of an inner wall of the pump housing (not shown). In this instance the rotor including blade 511 includes a flat working surface 512 (and not having a deformed surface therein) which is adapted for relative movement in the direction of the arrow shown with respect to the stepped formation 510 thereby to generate hydrodynamic thrust therebetween.

SEVENTH EMBODIMENT

Figure 26:
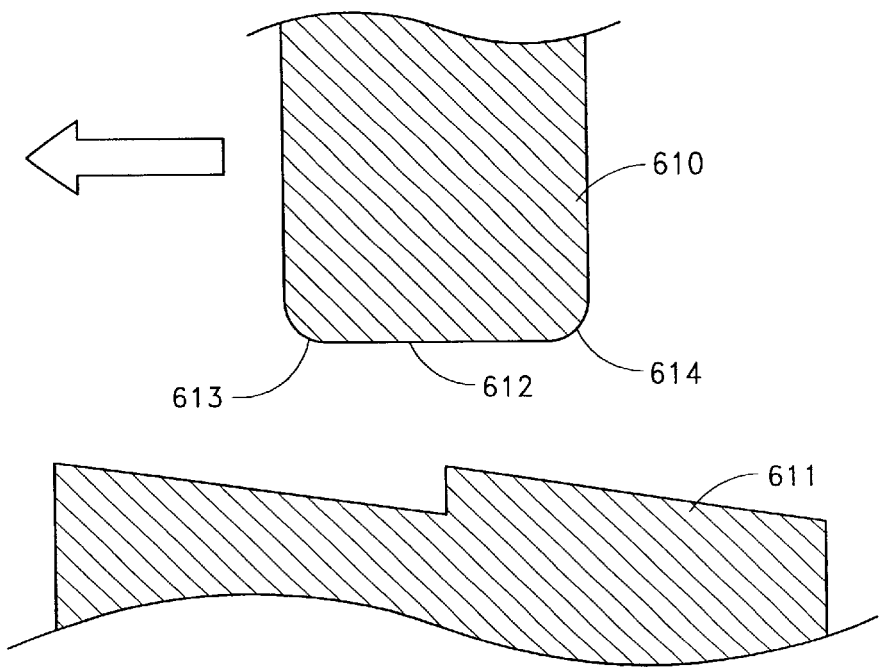
FIG. 26 illustrates a further embodiment wherein deformed surfaces are located both on the impeller and on the housing.

With reference to FIG. 26 there is shown an arrangement of rotor blade 610 with respect to stepped formation 611 and wherein the rotor blade 610 includes a deformed surface 612 at a working face thereof. In this instance the deformation comprises curved edges 613, 614. As for the previous embodiment relative movement of the rotor blade 610 in the direction of the arrow with respect to deformed surface 611 forming part of the pump housing (not shown) causes relative hydrodynamic thrust therebetween.

The foregoing describes principles and examples of the present invention, and modifications, obvious to those skilled in the art, can be made thereto without departing from the scope and spirit of the invention.

PRINCIPLES OF OPERATION

Figure 27:
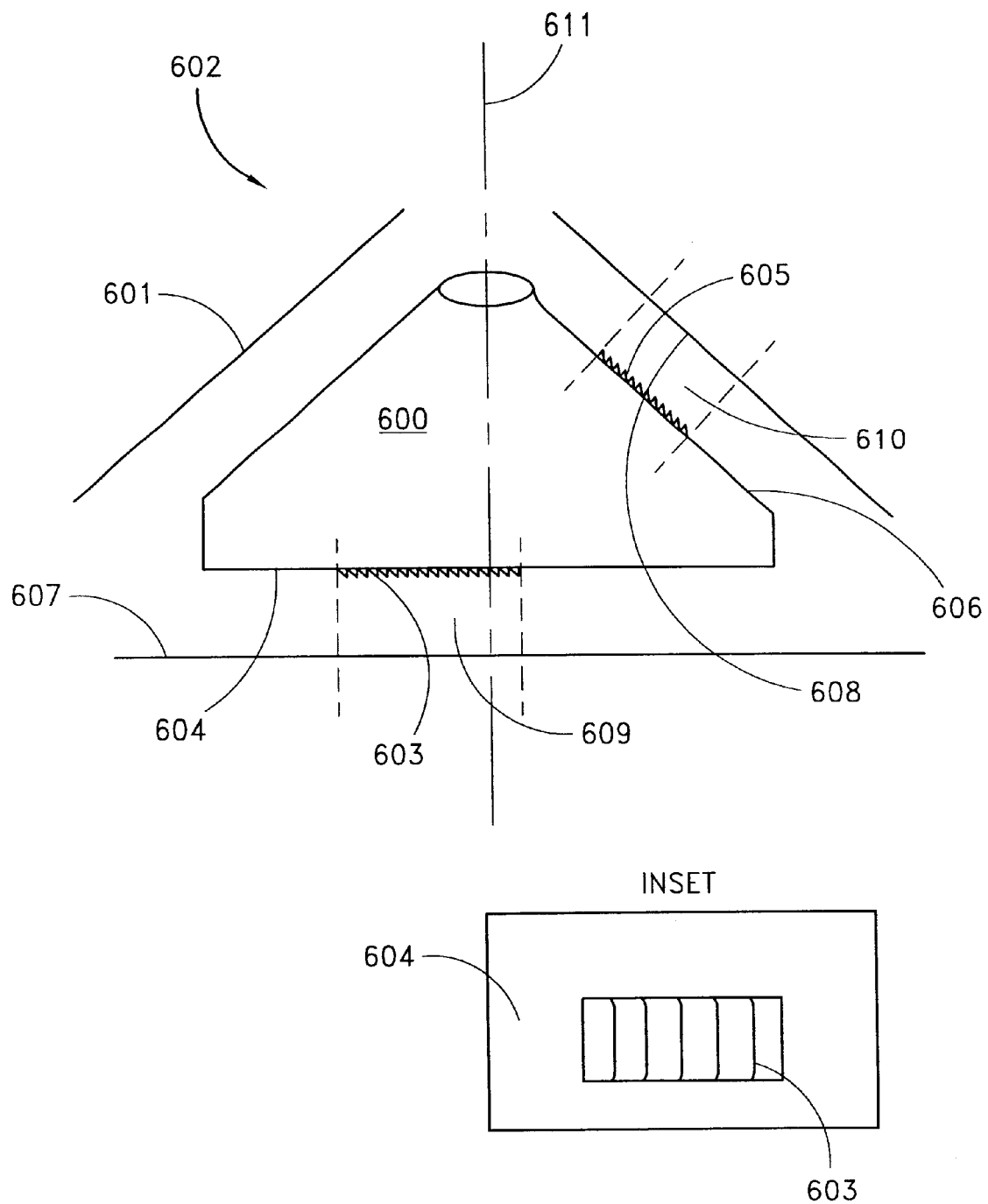
FIG. 27 illustrates diagramatically the basis of operation of the "deformed surfaces" utilised for hydrodymanic suspension of embodiments of the invention.

With particular reference to FIG. 27 this specification describes the suspension of an impeller 600 within a pump housing 601 by the use of hydrodynamic forces. In this specification the suspension of the impeller 600 is performed dominantly which is to say exclusively by hydrodynamic forces.

The hydrodynamic forces are forces which are created by relative movement between two surfaces which have a fluid in the gap between the two surfaces. In the case of the use of the pump assembly 602 as a rotary blood pump the fluid is blood.

The hydrodynamic forces can arise during relative movement between two surfaces even where those surfaces are substantially entirely parallel to each other or non-deformed. However, in this specification, hydrodynamic forces are caused to arise during relative movement between two surfaces where at least one of the surfaces includes a "deformed surface".

In this specification "deformed surface" means a surface which includes an irregularity relative to a surface which it faces such that, when the surface moves in a predetermined direction relative to the surface which it faces the fluid located in the gap there between experiences a change in relative distance between the surfaces along the line of movement thereby to cause a hydrodynamic force to arise therebetween in the form of a thrust force including at least a component substantially normal to the plane of the gap defined at any given point between the facing surfaces.

In the example of FIG. 27 there is a first deformed surface 603 forming at least part of a first face 604 of impeller 600 and a second deformed surface 605 on a second face 606 of the impeller 600.

The inset of FIG. 27 illustrates conceptually how the first deformed surface 603 may form only part of the first face 604.

The first deformed surface 603 faces first inner surface 607 of the pump housing 601 whilst second deformed surface 605 faces second inner surface 608 of the pump housing 601.

In use first gap 609 defined between first deformed surface 603 and first inner surface 607 has a fluid comprising blood located therein whilst second gap 610 defined between second deformed surface 605 and second inner surface 608 also has a fluid comprising blood located therein.

In use impeller 600 is caused to rotate about impeller axis 611 such that relative movement across first gap 609 between first deformed surface 603 and first inner face 607 occurs and also relative movement across second gap 610 between second deformed surface 605 and second inner surface 608 occurs. The orientation of the deformities of first deformed surface 603 and second deformed surface 605 relative to the line of movement of the deformed surfaces 603, 605 relative to the inner surfaces 607, 608 is such that the fluid in the gaps 609, 610 experiences a change in height of the gap 609, 610 as a function of time and with the rate of change dependant on the shape of the deformities of the deformed surfaces and also the rate of rotation of the impeller 600 relative to the housing 601. That is, at any given point on either inner surface 607 or 608, the height of the gap between the inner surface 607 or 608 and corresponding deformed surface 603 or 605 will vary with time due to passage of the deformed surface 603 or 605 over the inner surface.

Hydrodynamic forces in the form of thrust forces normal to the line of relative movement of the respective deformed surfaces 603, 605 relative to the inner surfaces 607, 608 thus arise.

With this configuration it will be noted that the first gap 609 lies substantially in a single plane whilst the second gap 610 is in the form of a cone and angled at an acute angle relative to the plane of the first gap 609.

Accordingly, the thrust forces which can be enlisted to first gap 609 and second gap 610 are substantially normal to and distributed across both the predominantly flat plane of first deformed surface 603 and normal to the substantially conical surface of second deformed surface 605 thereby permitting restoring forces to be applied between the impeller 600 and the pump housing 601 thereby to resist forces which seek to translate the impeller 600 in space relative to the pump housing 601 and also to rotate the impeller 600 about any axis (other than about the impeller axis 611) relative to the pump housing 601. This arrangement substantially resists five degrees of freedom of movement of impeller 600 with respect to the housing 601 and does so predominantly without any external intervention to control the position of the impeller with respect to the housing given that disturbing forces from other sources, most notably magnetic forces on the impeller due to its use as rotor of the motor are net zero when the impeller occupies a suitable equilibrium position. The balance of all forces on the rotor, effected by manipulation of magnetic and other external sources, may be adjusted such that the rotor is predominantly hydrodynamically born.

It will be observed that these forces increase as the gaps 609, 610 narrow relative to a defined operating position and decrease as the gaps 609, 610 increase relative to a defined operating gap. Because of the opposed orientation of first deformed surface 603 relative to second deformed surface 605 it is possible to design for an equilibrium position of the impeller 600 within the pump housing 601 at a defined equilibrium gap distance for gaps 609, 610 at a specified rotor rotational speed about axis 611 and rotor mass leading to a close approximation to an unconditionally stable environment for the impeller 600 within the pump housing 601 against a range of disturbing forces.

Characteristics and advantages which flow from the arrangement described above and with reference to the embodiments includes:

1. Low haemolysis, hence low running speed and controlled fluid dynamics (especially shear stress) in the gap between the casing and impeller. This in turn led to the selection of radial off-flow and minimal incidence at on-flow to the rotor;

2. Radial or near-radial off-flow from the impeller can be chosen in order to yield a "flat" pump characteristic (HQ) curve.

INDUSTRIAL APPLICABILITY

The pump assembly 1, 200 is applicable to pump fluids such as blood on a continuous basis. With its expected reliability it is particularly applicable as an in vivo heart assist pump.

The pump assembly can also be used with advantage for the pumping of other fluids where damage to the fluid due to high shear stresses must be avoided or where leakage of the fluid must be prevented with a very high degree of reliability—for example where the fluid is a dangerous fluid.

What is claimed is:

1. A rotary blood pump for use in a heart assist device or like device, said pump having an impeller suspended in use within a pump housing exclusively by hydrodynamic thrust forces generated by relative movement of said impeller with respect to and within said pump housing; and wherein at least one of said impeller or said housing includes at least a first deformed surface lying on at least part of a first face and a second deformed surface lying on at least part of a second face which, in use, move relative to respective facing surfaces on the other of said impeller or said housing thereby to form at least two relatively moving surface pairs which generate relative hydrodynamic thrust between said impeller and said housing which includes everywhere a localized thrust component substantially and everywhere normal to the plane of movement of said first deformed surface and said second deformed surface with respect to said facing surfaces; and wherein the combined effect of the localized normal forces generated on the surfaces of said impeller is to produce resistive forces against movement in three translational and two rotational degrees of freedom thus supporting the impeller for rotational movement within said housing exclusively by hydrodynamic forces.

2. The pump of claim 1 wherein at least one of said impeller or said housing includes at least one deformed surface which, in use, moves relative to a facing surface on the other of said impeller or said housing thereby to cause a restriction in the form of a reducing distance between the surfaces with respect to the relative line of movement of said deformed surface thereby to generate relative hydrodynamic thrust between said impeller and said housing which includes everywhere a localized thrust component substantially and everywhere normal to the plane of movement of said deformed surface with respect to said facing surface.

3. The pump of claim 2 wherein the combined effect of the localized normal forces generated on the surfaces of said impeller is to produce resistive forces against movement in three translational and two rotational degrees of freedom thus supporting the impeller for rotational movement within said housing exclusively by hydrodynamic forces.

4. The blood pump of claim 1 wherein said thrust forces are generated by blades of said impeller.

5. The blood pump of claim 4 wherein said thrust forces are generated by edges of said blades of said impeller.

6. The blood pump of claim 5 wherein said edges of said blades are tapered or non-planar so that a thrust is created between the edges and the adjacent pump casing during relative movement therebetween.

7. The blood pump of claim 5 wherein said edges of said blades are shaped such that the gap at the leading edge of the blade is greater than at the trailing edge and thus the fluid which is drawn through the gap experiences a wedge shaped restriction which generates a thrust.

8. The blood pump of claim 1 wherein the pump is of centrifugal type or mixed flow type with impeller blades open on both front and back faces of said pump housing.

9. The blood pump of claim 1 wherein the front face of said pump housing is made conical, in order that the thrust perpendicular to a conical surface of said impeller has a radial component, which provides a radial restoring force to a radial displacement of the impeller axis during use.

10. The blood pump of claim 1 wherein the driving torque of said impeller derives from magnetic interaction between permanent magnets within blades of the impeller and oscillating currents in windings encapsulated in said pump housing.

11. The pump of claim 10 wherein said blades include magnetic material therein, the magnetic material encapsulated within a biocompatible shell or coating.

12. The pump of claim 11 wherein said biocompatible shell or coating comprises a diamond coating or other coating which can be applied at low temperature.

13. The pump of claim 11 wherein internal walls of said pump which can come into contact with said blades during use are coated with a hard material such as titanium nitride or diamond coating.

14. The pump of claim 1 wherein said impeller comprises an upper conical shroud having a taper or other deformed surface therein and wherein blades of said impeller are supported below said shroud.

15. The pump of claim 14 wherein said impeller further includes a lower shroud mounted in opposed relationship to said upper conical shroud and wherein said blades are supported within said upper conical shroud and said lower shroud.

16. The pump of claim 1 wherein said deformed surfaces are located on said impeller.

17. The pump of claim 1 wherein said deformed surfaces, are located on said housing.

18. The pump of claim 1 wherein forces imposed on said impeller in use, other than hydrodynamic forces, are controlled by design so that, over a predetermined range of operating parameters, said hydrodynamic thrust forces provide sufficient thrust to maintain said impeller suspended in use within said pump housing.

19. The blood pump of claim 1 wherein said first deformed surface lies on at least part of a first face of said impeller.

20. The blood pump of claim 1 wherein said second deformed surface lies on a second face of said impeller.

21. The blood pump of claim 1 wherein said first deformed surface lies on a first inner face of said housing.

22. The blood pump of claim 1 wherein said second deformed surface lies on a second inner face of said housing.

23. The blood pump of claim 1 wherein said first deformed surface covers entirely said first face.

24. The blood pump of claim 1 wherein said first deformed surface covers entirely said second face.

25. The blood pump of claim 1 wherein said first face lies at an acute angle relative to said second face.

26. The blood pump of claim 1 wherein said first deformed surface comprises deformations in said first face of said impeller whereby a gap between said first deformed surface and a first facing surface on said housing forms, in use, a restriction in the form of a reducing distance between the surfaces with respect to the relative line of movement of said first deformed surface.

27. The blood pump of claim 26 wherein said gap takes the form of a wedge shaped restriction which generates a thrust in use.

28. A rotary blood pump for use in a heart assist device or like device, said pump having an impeller suspended in use within a pump housing by hydrodynamic thrust forces generated by relative movement of said impeller with respect to and within said pump housing; and wherein at least one of said impeller or said housing includes at least a first deformed surface lying on at least part of a first face and a second deformed surface lying on at least part of a second face which, in use, move relative to respective facing surfaces on the other of said impeller or said housing thereby to form at least two relatively moving surface pairs which generate relative hydrodynamic thrust between said impeller and said housing which includes everywhere a localized thrust component substantially and everywhere normal to the plane of movement of said first deformed surface and said second deformed surface with respect to said facing surfaces; and wherein the combined effect of the localized normal forces generated on the surfaces of said impeller is to produce resistive forces against movement in three translational and two rotational degrees of freedom thus supporting the impeller for rotational movement within said housing by hydrodynamic forces.

29. The blood pump of claim 28 wherein said first deformed surface lies on at least part of a first face of said impeller.

30. The blood pump of claim 28 wherein said second deformed surface lies on a second face of said impeller.

31. The blood pump of claim 28 wherein said first deformed surface lies on a first inner face of said housing.

32. The blood pump of claim 28 wherein said second deformed surface lies on a second inner face of said housing.

33. The blood pump of claim 28 wherein said first deformed surface covers entirely said first face.

34. The blood pump of claim 28 wherein said first deformed surface covers entirely said second face.

35. The blood pump of claim 28 wherein said first face lies at an acute angle relative to said second face.

36. The blood pump of claim 28 wherein said hydrodynamic forces are augmented by other forces to support said impeller for rotation within said housing.

37. The blood pump of claim 36 wherein said other forces include magnetic forces.

38. The blood pump of claim 28 wherein said first deformed surface comprises deformations in said first face of said impeller whereby a gap between said first deformed surface and a first facing surface on said housing forms, in use, a restriction in the form of a reducing distance between the surfaces with respect to the relative line of movement of said first deformed surface.

39. The blood pump of claim 38 wherein said gap takes the form of a wedge shaped restriction which generates a thrust in use.

40. The blood pump of claim 28 wherein the pump is of centrifugal type or mixed flow type with impeller blades open on both front and back faces of said pump housing.

41. The blood pump of claim 28 wherein the front face of said pump housing is made conical, in order that the thrust perpendicular to a conical surface of said impeller has a radial component, which provides a radial restoring force to a radial displacement of the impeller axis during use.

42. The blood pump of claim 28 wherein the driving torque of said impeller derives from magnetic interaction between permanent magnets within blades of the impeller and oscillating currents in windings encapsulated in said pump housing.

43. The pump of claim 42 wherein said blades include magnetic material therein, the magnetic material encapsulated within a biocompatible shell or coating.

44. The pump of claim 43 wherein said biocompatible shell or coating comprises a diamond coating or other coating which can be applied at low temperature.

45. The pump of claim 43 wherein internal walls of said pump which can come into contact with said blades during use are coated with a hard material such as titanium nitride or diamond coating.

46. The pump of claim 28 wherein said impeller comprises an upper conical shroud having a taper or other deformed surface therein and wherein blades of said impeller are supported below said shroud.

47. The pump of claim 46 wherein said impeller further includes a lower shroud mounted in opposed relationship to said upper conical shroud and wherein said blades are supported within said upper conical shroud and said lower shroud.

48. The pump of claim 28 wherein said deformed surfaces are located on said impeller.

49. The pump of claim 28 wherein said deformed surfaces are located on said housing.

* * * * *

UNITED STATES PATENT AND TRADEMARK OFFICE
CERTIFICATE OF CORRECTION

PATENT NO.    : 6,250,880 B1
DATED         : June 26, 2001
INVENTOR(S)   : Woodard et al.

It is certified that error appears in the above-identified patent and that said Letters Patent is hereby corrected as shown below:

<u>Title page,</u>
Item [73], Assignee should read -- Ventrassist Pty. Ltd. Labrador, Queensland, Australia and University of Sydney Technology, New South Wales, Austrailia --

Signed and Sealed this

Twentieth Day of August, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,250,880 B1
DATED : June 26, 2001
INVENTOR(S) : Woodard et al.

It is certified that error appears in the above-identified patent and that said Letters Patent is hereby corrected as shown below:

<u>Title page,</u>
Item [63], please replace "Continuation of application No. PCT/AU98/00725, filed on Sep. 18, 1998" with -- Continuation of application No. PCT/AU98/00725, filed on Sep. 7, 1998 --.

Signed and Sealed this

Eighth Day of April, 2003

JAMES E. ROGAN
*Director of the United States Patent and Trademark Office*